(12) United States Patent
Brady et al.

(10) Patent No.: US 10,107,768 B2
(45) Date of Patent: Oct. 23, 2018

(54) VOLUMETRIC-MOLECULAR-IMAGING SYSTEM AND METHOD THEREFOR

(71) Applicant: Duke University, Durham, NC (US)

(72) Inventors: David Jones Brady, Durham, NC (US); Joel Alter Greenberg, Durham, NC (US); Shuo Pang, Durham, NC (US); Kenneth Patrick MacCabe, Raleigh, NC (US)

(73) Assignee: Duke University, Durham, NC (US)

( * ) Notice: Subject to any disclaimer, the term of this patent is extended or adjusted under 35 U.S.C. 154(b) by 236 days.

(21) Appl. No.: 14/912,014

(22) PCT Filed: Aug. 13, 2014

(86) PCT No.: PCT/US2014/050872
§ 371 (c)(1),
(2) Date: Feb. 12, 2016

(87) PCT Pub. No.: WO2015/023741
PCT Pub. Date: Feb. 19, 2015

(65) Prior Publication Data
US 2016/0187269 A1    Jun. 30, 2016

Related U.S. Application Data

(60) Provisional application No. 61/865,258, filed on Aug. 13, 2013.

(51) Int. Cl.
| G01N 23/201 | (2018.01) |
| G01N 23/207 | (2018.01) |
| G01N 23/20008 | (2018.01) |

(52) U.S. Cl.
CPC ..... *G01N 23/207* (2013.01); *G01N 23/20008* (2013.01)

(58) Field of Classification Search
CPC .... G01N 23/201; G01N 23/203; G01N 23/20; G01V 5/0025; A61B 6/483
See application file for complete search history.

(56) References Cited

U.S. PATENT DOCUMENTS

| 3,971,065 A | 7/1976 | Bayer |
| 5,048,959 A | 9/1991 | Morris et al. |

(Continued)

FOREIGN PATENT DOCUMENTS

| GB | 2441162 A | 2/2008 |
| WO | 2013103408 A1 | 7/2013 |

(Continued)

OTHER PUBLICATIONS

International Preliminary Report on Patentability, dated Feb. 25, 2016, issued in counterpart International Patent Application No. PCT/US2014/050872.

(Continued)

*Primary Examiner* — Don Wong
(74) *Attorney, Agent, or Firm* — Kaplan Breyer Schwarz, LLP

(57) ABSTRACT

An imaging system operative for providing a volumetric molecular image of an object is disclosed. The imaging system interrogates the object with structured x-ray radiation while continuous relative motion between the object and source is induced during a measurement period. As the radiation passes through the object, the radiation scatters based on the molecular composition within the object, and the scattering changes as a function of time due to the relative motion between the source and object. Coherent scatter radiation is detected and processed to reconstruct an estimate of the three-dimensional molecular structure of the object using a reconstruction algorithm, such as maximum likelihood estimation.

19 Claims, 13 Drawing Sheets

(56) References Cited

U.S. PATENT DOCUMENTS

| | | | |
|---|---|---|---|
| 5,157,298 A | 10/1992 | Kawabata | |
| 5,627,639 A | 5/1997 | Mende et al. | |
| 5,940,468 A | 8/1999 | Huang et al. | |
| 6,122,051 A | 9/2000 | Ansley et al. | |
| 6,205,195 B1 | 3/2001 | Lanza | |
| 6,392,235 B1 | 5/2002 | Barrett et al. | |
| 6,950,492 B2 | 9/2005 | Besson | |
| 7,265,698 B2 | 9/2007 | Fackenthal et al. | |
| 7,283,231 B2 | 10/2007 | Brady et al. | |
| 7,301,625 B2 | 11/2007 | Brady et al. | |
| 7,336,353 B2 | 2/2008 | Brady et al. | |
| 7,427,932 B2 | 9/2008 | Brady et al. | |
| 7,432,843 B2 | 10/2008 | Brady et al. | |
| 7,463,174 B2 | 12/2008 | Brady et al. | |
| 7,463,179 B2 | 12/2008 | Brady et al. | |
| 7,532,772 B2 | 5/2009 | Brady | |
| 7,573,579 B2 | 8/2009 | Brady | |
| 7,580,499 B2 | 8/2009 | Van Stevendaal et al. | |
| 7,583,783 B2 | 9/2009 | Harding | |
| 7,616,306 B2 | 11/2009 | Brady et al. | |
| 7,623,614 B2 | 11/2009 | Shefsky | |
| 7,835,495 B2 | 11/2010 | Harding | |
| 7,912,173 B2 | 3/2011 | Brady | |
| 8,149,400 B2 | 4/2012 | Brady et al. | |
| 8,338,793 B2 | 12/2012 | DeVito | |
| 8,553,222 B2 | 10/2013 | Brady et al. | |
| 8,928,988 B1 | 1/2015 | Ford et al. | |
| 8,932,894 B2 | 1/2015 | Christophersen et al. | |
| 9,013,554 B2 | 4/2015 | Brady et al. | |
| 9,335,281 B2 * | 5/2016 | Marks | G01N 23/201 |
| 9,432,591 B2 | 8/2016 | Brady et al. | |
| 9,473,700 B2 | 10/2016 | Cossairt et al. | |
| 9,482,850 B2 | 11/2016 | Ford et al. | |
| 2002/0135885 A1 | 9/2002 | Chen et al. | |
| 2003/0095631 A1 | 5/2003 | Rosner | |
| 2004/0076319 A1 | 4/2004 | Fauver et al. | |
| 2005/0052751 A1 | 3/2005 | Liu et al. | |
| 2005/0174573 A1 | 8/2005 | Harvey et al. | |
| 2006/0038705 A1 | 2/2006 | Brady et al. | |
| 2006/0072109 A1 | 4/2006 | Bodkin et al. | |
| 2007/0047424 A1 | 3/2007 | Wada et al. | |
| 2007/0296965 A1 | 12/2007 | Brady et al. | |
| 2007/0296969 A1 | 12/2007 | Goldstein et al. | |
| 2008/0074663 A1 | 3/2008 | Brady et al. | |
| 2008/0095298 A1 | 4/2008 | Shefsky | |
| 2009/0201498 A1 | 8/2009 | Raskar et al. | |
| 2010/0177864 A1 | 7/2010 | Donath et al. | |
| 2010/0215142 A1 | 8/2010 | Dafni et al. | |
| 2011/0019068 A1 | 1/2011 | Chiu | |
| 2011/0190616 A1 | 8/2011 | Marwala et al. | |
| 2011/0282181 A1 | 11/2011 | Wang et al. | |
| 2012/0105844 A1 | 5/2012 | Brady et al. | |
| 2013/0021392 A1 | 1/2013 | Travis | |
| 2013/0250124 A1 | 9/2013 | Furry | |
| 2014/0247920 A1 | 9/2014 | Marks et al. | |
| 2015/0116553 A1 | 4/2015 | Ford et al. | |
| 2015/0207990 A1 | 7/2015 | Ford et al. | |
| 2015/0351705 A1 * | 12/2015 | Brady | G01N 23/046 378/20 |
| 2016/0187269 A1 | 6/2016 | Brady et al. | |

FOREIGN PATENT DOCUMENTS

| | | | |
|---|---|---|---|
| WO | 2014121039 A1 | 8/2014 | |
| WO | 2015/023741 A1 | 2/2015 | |

OTHER PUBLICATIONS

"Office Action" dated Jan. 9, 2017 issued related in U.S. Appl. No. 14/764,435.

"Final Office Action" U.S. Appl. No. 14/764,435, dated Jul. 10, 2017, 9 pp.

Officer: Shane Thomas, "International Search Report & Written Opinion of the International Searching Authority"; issued in related International Application No. PCT/US2012/058744, dated Jun. 17, 2013.

Athina Nickitas-Etienne, "International Preliminary Report on Patentability", issued in related International Application No. PCT/US2012/058744, dated Apr. 17, 2014.

"International Search Report & Written Opinion of the International Searching Authority"; issued in related International Application No. PCT/US2014/014087, dated Apr. 30, 2014.

"International Preliminary Report on Patentability", issued in related International Application No. PCT/US2014/0140897, dated Aug. 4, 2015.

"International Search Report and Written Opinion of the International Searching Authority", issued in International Application No. PCT/US2014/050872 dated Dec. 1, 2014.

Choi, et al., "Coded Aperture Computed Tomography", "Adaptive Coded Imagine, Non-Imaging, and Unconventional Imaging Sensor Systems", 2009, pp. 1-10, vol. 7468, No. 74680B, Publisher: SPIE; doi: 10.1117/12.825277.

Greenberg, et al., "Structured illumination for tomographic X-ray diffraction imaging", "Analyst", Dec. 4, 2013, pp. 709-713, vol. 139, Publisher: The Royal Society of Chemistry; DOI: 10.1039/c3an01641b.

Harding, et al., "Automatic detection of explosives in airline baggage using elastic X-ray scatter", "medicamundi", Jul. 1998, pp. 30-33, vol. 42, No. 2.

MacCabe, et al., "Pencil beam coded aperture x-ray scatter imaging", "Optics Express", Jul. 16, 2012, pp. 16310-16320, vol. 20, No. 15, Publisher: OSA, Published in: US.

Mrozack, et al., "Coded aperture spectroscopy with denoising through sparsity", "Optics Express", Jan. 16, 2012, pp. 2297-2309, vol. 20, No. 2, Publisher: OSA, Published in: US.

William Hadley Richardson, "Bayesian-Based Iterative Method of Image Restoration", Jan. 1972, pp. 55-59, vol. 62, No. 1, Publisher: Journal of the Optical Society of America, Published in: US.

Westmore, et al., "Tomographic imaging of the angular-dependent coherent-scatter cross section", "Medical Physics", Jan. 1997, pp. 1-10, vol. 24, No. 1, Publisher: American Association of Physicists in Medicine.

Dicken, et al., "Combined X-ray diffraction and kinetic depth effect imaging", "Optics Express", Mar. 21, 2011, pp. 6406-6413, vol. 19, No. 7, Publisher: Optical Society of America.

Westmore, et al., "Angular-dependent coherent scatter measured with a diagnostic x-ray image intensifier-based imaging system", "Medical Physics", Feb. 19, 1996, pp. 723-733, vol. 23, No. 5, Publisher: American Association of Physicists in Medicine, Published in: CA.

"Notice of Allowance" dated Mar. 1, 2018 in U.S. Appl. No. 14/764,435.

Wagadarikar et al., "Single disperser for coded aperture snapshot spectral imaging", "Applied Optics", dated Apr. 1, 2008, p. B44-B51, vol. 47, No. 10, Publisher. Optical Society of America.

In't Zand et al., "The optimum open fraction of coded apertures. With an application to the wide field X-ray cameras of SAX", "Astronomy and Physics", dated Jan. 31, 1994, p. 665-674, vol. 288.

Gehm et al., "Single-shot compressive spectral imaging with a dual-disperser architecture", "Optics Express", dated Oct. 17, 2007, pp. 14013-14027, vol. 15, No. 21.

"Non-Final Office Action", Related U.S. Appl. No. 15/351,077, dated Mar. 23, 2017, 10 pp.

"Non-Final Office Action", U.S. Appl. No. 13/340,893 dated Feb. 7, 2013, 11 pp.

"Non-Final Office Action", U.S. Appl. No. 12/422,031 dated Sep. 22, 2011, p. 9, Publisher: USPTO.

"Non-Final Office Action", U.S. Appl. No. 13/407,047, dated Sep. 24, 2014, 9 pp.

"Notice of Allowance and Fees Due", U.S. Appl. No. 14/350,073, dated Jan. 12, 2016, 7 pp.

"Non-Final Office Action", U.S. Appl. No. 14/350,073, dated Aug. 17, 2015, 13 pp.

* cited by examiner

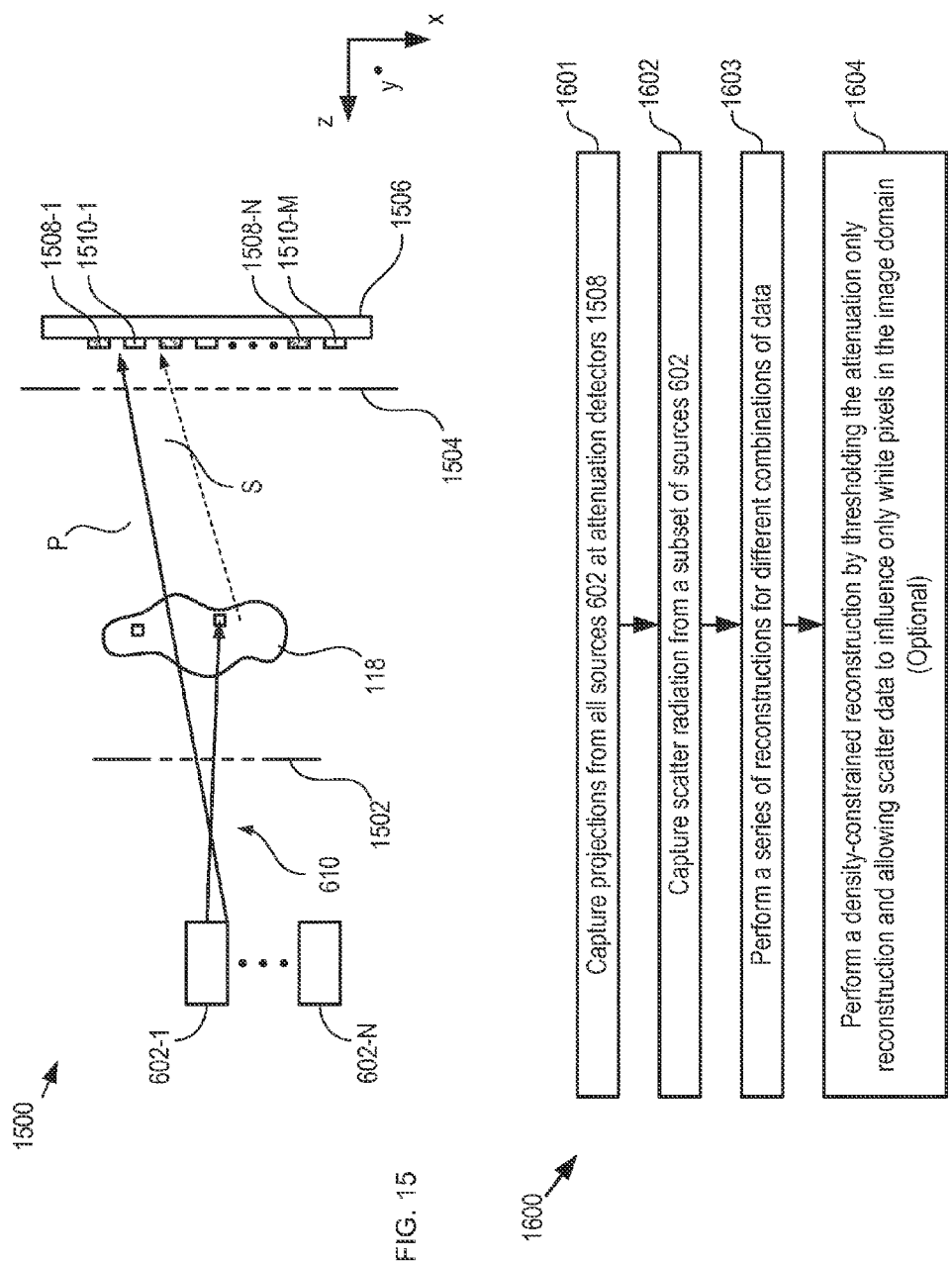

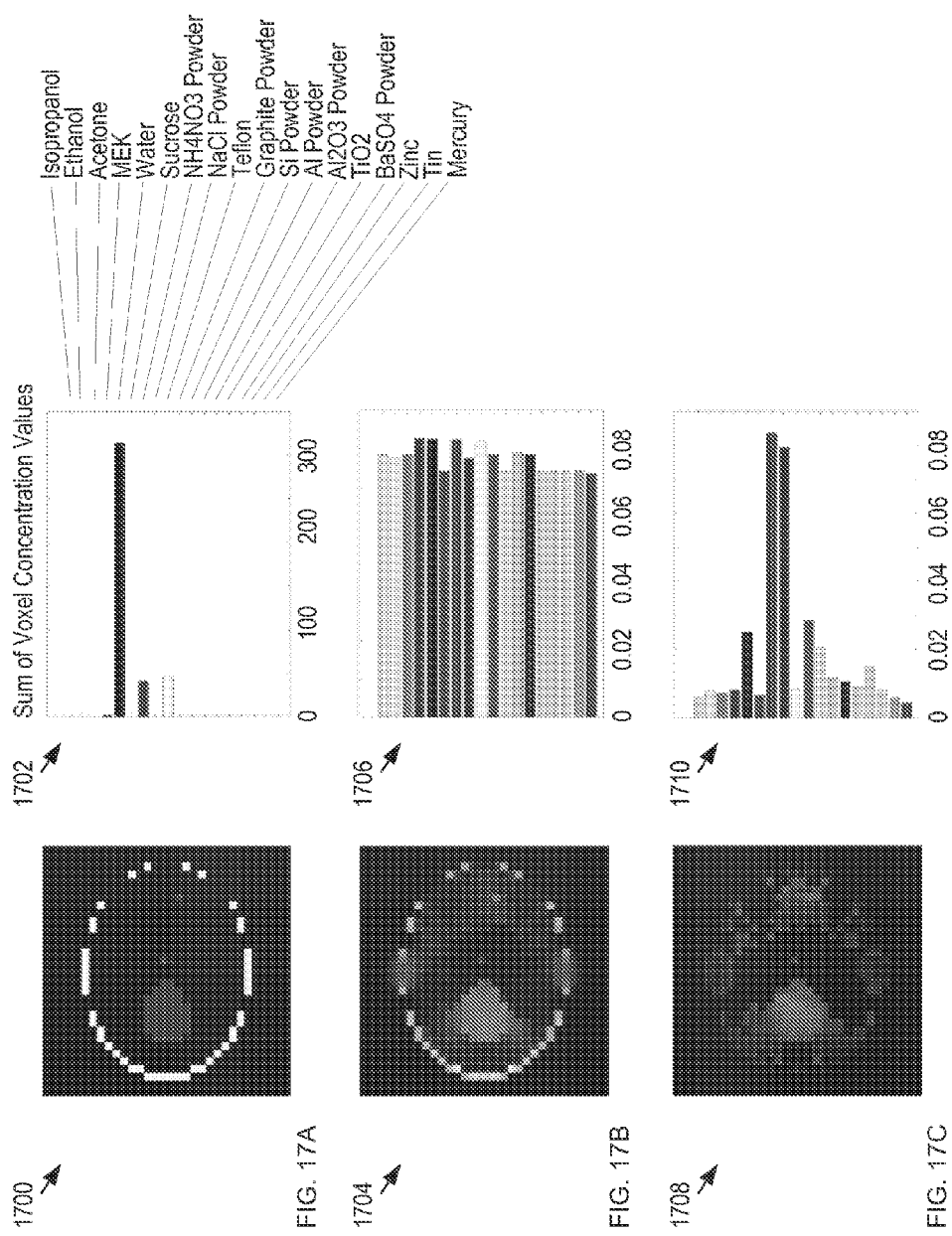

VOLUMETRIC-MOLECULAR-IMAGING SYSTEM AND METHOD THEREFOR

CROSS REFERENCE TO RELATED APPLICATIONS

This application claims the benefit of U.S. Provisional Application Ser. No. 61/865,258, filed Aug. 13, 2013, entitled "Systems and Methods for Structured Illumination for Volumetric Molecular Imaging,", which is incorporated by reference. If there are any contradictions or inconsistencies in language between this application and one or more of the cases that have been incorporated by reference that might affect the interpretation of the claims in this case, the claims in this case should be interpreted to be consistent with the language in this case.

STATEMENT REGARDING FEDERALLY SPONSORED RESEARCH

This invention was made with Government support under HSHQDC-11-C-00083 awarded by the Department of Homeland Security. The Government has certain rights in the invention.

FIELD OF THE INVENTION

The present invention relates to x-ray diffraction imaging in general, and, more particularly, to the use of x-ray diffraction for volumetric molecular imaging.

BACKGROUND OF THE INVENTION

Volumetric molecular imaging to determine the chemical composition of an object has become critically important in a number of application areas, such as homeland defense, port inspection, and airport security. Promising techniques for performing such analysis include interrogation of the object with x-ray radiation, which has been relied upon for years to provide insight into the structure of objects in the areas of baggage inspection, medical imaging, and semiconductor crystal analysis, among others.

X-rays can interact with materials in a number of ways, including photoelectric absorption, Compton scatter, coherent (Bragg) scatter and fluorescence. Historically, conventional x-ray inspection systems have been used only to measure variations in the manner in which the x-rays propagate through an object (e.g., absorption). Unfortunately, this does not provide information about molecular or atomic identity.

The chemical composition information about molecular or atomic identity information can be obtained by analyzing the scatter behavior of x-rays directed at an object, however. There exists a well-known relationship between a material's molecular structure and the angle at which a given x-ray will scatter from it. As a result, the molecular structure a material gives rise to unique scattering behavior, such that each material has a scatter "signature" that can be used to identify it. In recent years, a number of techniques have been developed to exploit this phenomenon.

Coherent scatter computed tomography (CSCT) is one such approach for providing molecular imaging capability. In a typical CSCT system, a poly-energetic x-ray beam, typically pencil-shaped, is directed at an object to give rise to low-angle coherent-scatter x-ray diffraction. The scatter radiation is then detected and used to identify the molecular structure. Examples of CSCT systems are found in, for example, U.S. Pat. No. 7,580,499, "Energy-dispersive coherent scatter computed tomography, *Applied Physics Letters*, 88(24):243506 (2006), "Angular-dependent coherent scatter measured with a diagnostic x-ray image intensifier-based imaging system," *Medical Physics*, 23(5):723-733 (1996), and "x-ray diffraction computed tomography," *Medical Physics*, 14(4):515-525, (1987).

Another approach to molecular imaging is energy dispersive x-ray diffraction tomography (EXDT), examples of which are disclosed in U.S. Pat. No. 7,835,495 and "Energy-dispersive x-ray diffraction tomography," *Physics in Medicine and Biology*, 35(1):33 (1990). In this approach, a fan-shaped x-ray beam and a plurality of pencil-shaped x-ray beams are directed at an object and the scatter radiation is received at a plurality of detectors that includes a transmission detector array and a plurality of scatter detectors. Information about the molecular composition of the object is generated from the output signals of all of the detectors.

Other prior-art approaches include kinetic-depth-effect x-ray diffraction (KDEXRD), which is disclosed in "Combined x-ray diffraction and kinetic depth effect imaging," *Optics Express*, 19(7):6406-6413, (2011), and coded-aperture x-ray scatter imaging (CAXSI), disclosed in "Pencil beam coded aperture x-ray scatter imaging," *Optics Express*, 20(15):16310-16320 (2012).

Each of these approaches, however, have drawbacks that limit their practical utility. For example, poor utilization of the incident photons gives rise to a weak coherent scatter signal. In addition, therefore, many of these approaches result in the capture of the scatter from only a small fraction of the radiation directed at the scanned object and are, therefore, highly inefficient. As a result, in order to produce an output signal having sufficiently high SNR over a short time, they require either x-ray sources capable of high power to increase the available radiation at the detector, or long exposure times. In either case, this exposes the scanned object to excessive amounts of x-ray radiation, which can be undesirable in many applications. Further, prior-art systems rely on the use of pencil or fan beams to sequentially interrogate small sections (e.g., a single voxel or planar slice) at a time, which can be very time consuming. The need to develop the tomographic model of the object one portion at time can lead to an undesirable space-time spectral trade-off.

As a result, it is difficult, at best, to employ such approaches in a real-time molecular imaging system. There remains a need, therefore, for an improved imaging system that noninvasively ascertains the structural and molecular composition of three-dimensional objects at high speed and with relatively lower cost and complexity.

SUMMARY OF THE INVENTION

The present invention enables volumetric molecular imaging without some of the disadvantages of the prior art. Embodiments of the present invention are particularly well suited for use in applications where the knowledge of the three-dimensional shape and composition of an object is advantageous—for example, medical imaging, security (e.g., baggage inspection, etc.), structural integrity verification, and homeland defense (e.g., customs, weapons inspection, port security, etc.).

The present invention enables the development of a volumetric molecular image of an object via coherent scatter imaging by interrogating the object with a structured x-ray radiation pattern while the interaction between the object and the structured radiation pattern is changed as a function of time (for example, by moving the object through the radiation pattern during the measurement). As the radiation passes through the object, it scatters based on the molecular composition within the object, and the scattering has a time dependency due to the changing interaction between the radiation and the object. The scattered radiation is detected at a detector having one or more energy-sensitive detector elements and the scatter information is processed to reconstruct an estimate of the three-dimensional molecular structure of the object using a reconstruction algorithm, such as a maximum likelihood estimation.

Like some prior-art molecular imaging systems, embodiments of the present invention interrogate an object with a spatially modulated x-ray radiation beam. In such prior-art systems, a three-dimensional estimation of the molecular structure of the object is developed by sequentially analyzing two-dimensional "slices" of the object taken while the object is stationary at different position and/or orientation with respect to the source. These slices are then combined into a three-dimensional volumetric image.

In contrast to the prior art, the present invention interrogates an object with a spatially modulated x-ray radiation pattern while the interaction between the object and the radiation is changed over time. As a result, scatter information is collected while each object voxel is illuminated in several different ways. This provides embodiments of the present invention with an N-fold (where N is the number of illumination events) enhancement of the scatter signal.

An illustrative embodiment of the present invention is a system for imaging an object, wherein the system comprises a source for providing x-ray radiation, a coded aperture for spatially modulating the x-ray radiation received by the object, a detector array for detecting x-ray radiation after it has passed through the object, and a stage for moving the object through the spatially modulated radiation while the object is being imaged. By monitoring the scattered radiation while the object is moving, the spatial modulation imparted by the coded aperture manifests a temporal modulation on the scattered radiation, thereby enabling a complete volumetric image of the molecular structure of the object to be developed in a single scan. As a result, embodiments of the present invention have one or more advantages over imaging systems of the prior art, including:
  i. reduced scan time; or
  ii. a reduction in the required incident photon flux; or
  iii. adaptive implementation; or
  iv. compressive implementation (i.e., N-dimensional object reconstruction with a M-dimensional detector, where M<N); or
  v. simultaneous limited-angle, transmission-based volumetric reconstruction of object density for improved material identification; or
  vi. mitigation of texturing; or
  vii. higher single-to-noise ratio; or
  viii. improved throughput; or
  ix. additional degrees of freedom in design; or
  x. any combination of i, ii, iii, iv, v, vi, vii, viii, or ix.

In some embodiments, the coded aperture has a code that imparts an amplitude modulation in at least one dimension. In some embodiments, the coded aperture is variable such that at least one parameter of the imaging system can be changed during a measurement to improve system performance.

In some embodiments a second coded aperture is included between the object and the detector array to structure the scattered radiation. In some embodiments, multiple coded apertures are located between the object and the detector array.

In some embodiments, multiple x-ray sources are used to simultaneously interrogate the object with multiple beams. In some of these embodiments, one or more collimators are included to substantially isolate one or more detectors from some of the x-ray sources.

In some embodiments, the object remains stationary and the source is moved to impart the time dependency on the scattered radiation.

In some embodiments, the source is a multi-source array that varies the characteristics of the illuminating radiation to impart the time-dependency on the scattered radiation.

An embodiment of the present invention is an imaging system operative for estimating the molecular structure of an object, the imaging system comprising: a first source that is operative for providing a first radiation beam; a first coded aperture, the first coded aperture being operative for spatially modulating the first radiation beam to provide a first plurality of beam elements; a means for changing the interaction between the first plurality of beam elements and the object in a time-dependent manner; and a detector that is operative for receiving radiation based on each of the plurality of beam elements, the detector including a first detector element that is an energy-sensitive detector element, the first detector element being arranged to receive scatter radiation from the object during the first time period, wherein the detector provides an output signal that is based on the received radiation, and wherein the output signal is a temporally resolved signal.

BRIEF DESCRIPTION OF THE DRAWINGS

FIG. 15 depicts a simplified schematic drawing of a portion of a molecular imaging system in accordance with third alternative embodiment of the present invention.

FIG. 16 depicts operations of a method suitable for reconstructing an image of an object based on both scatter and attenuation of x-ray radiation as it passes through the object.

FIGS. 17A, 17B, and 17C depict a modified Shepp-Logan phantom-based test object, a reconstruction using a density-constrained attenuation-only data set, and a reconstruction using a density-constrained attenuation and scatter data set, respectively.

DETAILED DESCRIPTION

Before delving into a detailed description of an illustrative embodiment of the present invention, an overview is provided here using a simple architecture that demonstrates the principles of the invention—namely, coherent-scatter imaging using structured illumination.

Overview

It has long been understood that Bragg's law expresses the relationship between a material's molecular structure, q, (which can be described in terms of the effective atomic spacing, d, of the material) and the angle at which an x-ray photon incident on the material will scatter from its initial propagation direction. The relationship between q and scatter angle, θ, for an x-ray photon with energy (E) can be expressed as:

$$q = \frac{1}{2d} = \frac{E}{hc}\sin(\theta/2), \quad (1)$$

where θ=2θ$_B$ (θ$_B$ is the Bragg scattering angle), h is Planck's constant, c is the speed of light in vacuum, and θ=½d is related to the momentum transferred to the photon upon scattering. Since every element has a unique atomic spacing, the scattering behavior of an object provides a unique signature for each of the molecular components within it. In other words, each value of d present in an object gives rise to scattered x-ray photons with a particular E(θ) relationship. In fact, knowledge of the molecular structure of an object provides a signature that is sufficiently unique that different materials within the object can be identified based solely on their momentum transfer spectra (referred to here as the structure function, f(q), which includes the observed values of d and their relative scatter strengths).

The present invention exploits this relationship to enable the molecular structure of an object to be distinguished based on the time, position, and energy-dependence of the measured scattered x-rays. Systems in accordance with the present invention interrogate an object with structured x-ray radiation while the interaction of the radiation and the object is changed such that it has a time dependency (e.g., by introducing a relative motion between the object and the source). As the radiation passes through the object, it scatters based on the molecular composition of features within the object. Due to the changing interaction between the illumination and the source, the scattering changes as a function of time. In addition, due to the structured illumination, each point in the object is illuminated several times in different ways during the measurement period. The scattered radiation is detected at a detector that includes one or more energy-sensitive detectors and the scatter information is processed to reconstruct an estimate of the three-dimensional molecular structure of the object.

Figure 1:
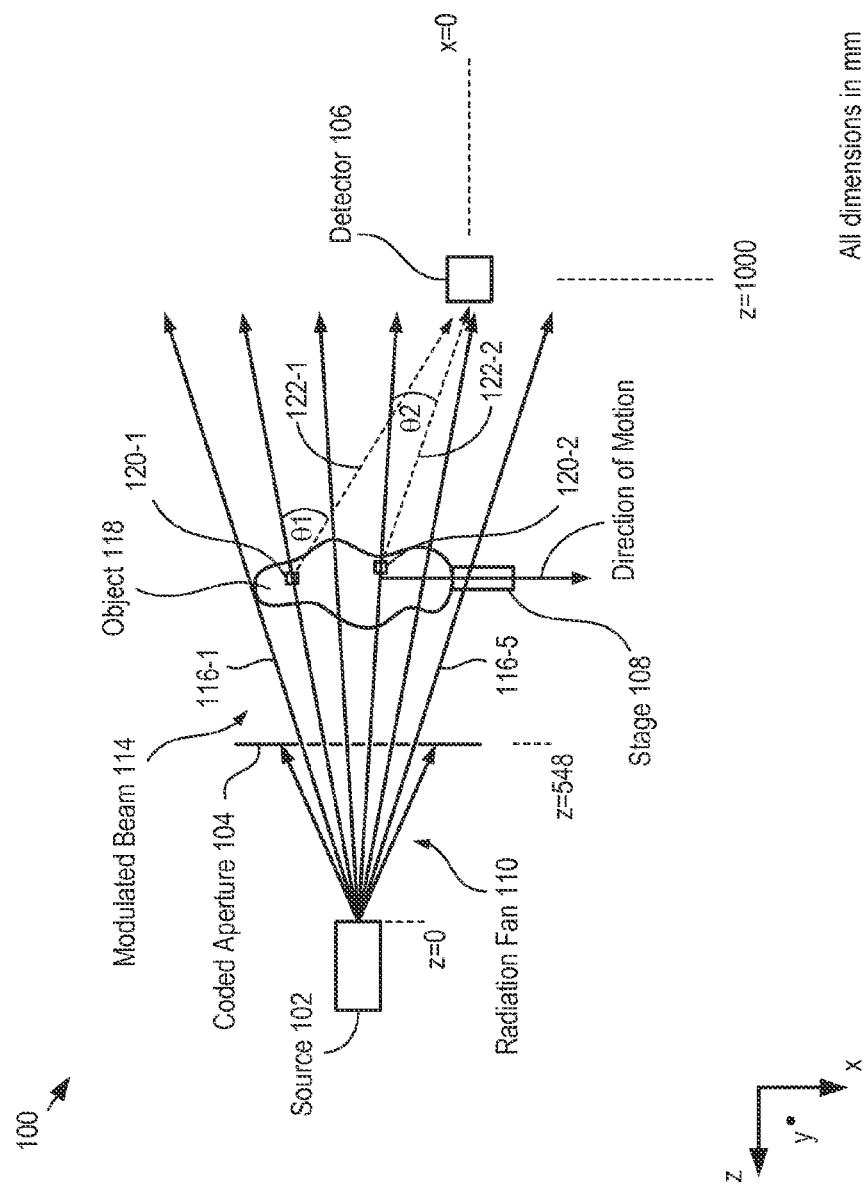
FIG. 1 depicts a schematic diagram of a simplified architecture that demonstrates the principles of coherent-scatter imaging using structured illumination.

FIG. 1 depicts a schematic diagram of a simplified architecture that demonstrates the principles of coherent-scatter imaging using structured illumination. System 100 is a molecular imaging system that interrogates a three-dimensional object (2 spatial dimensions and 1 material dimension) with a fan of pencil beams and detects the scatter radiation a single detector element. System 100 includes source 102, coded aperture 104, detector 106, and stage 108.

Source 102 is an x-ray radiation source that provides radiation fan 110 as a substantially fan-shaped beam of polychromatic x-ray radiation.

The radiation beam is spatially filtered at coded aperture 104 to provide modulated beam 114 as a periodic binary modulation of the fan beam such that scatter signals originating at different values of z yield orthogonal measurements. Coded aperture 104 includes a plurality of pinhole apertures arrayed in a line along the x-direction. As a result, modulated beam 114 includes a plurality of beam elements—specifically, primary beams 116-1 through 116-5, which are substantially pencil-shaped beams that diverge along a unique directions of propagation.

Detector 106 is a single-pixel, energy-sensitive x-ray radiation detector located to receive scatter radiation from the features of object 118.

In conventional fashion, object 118 (the object under test) is represented as a three-dimensional arrangement of volume pixels (referred to as "voxels"). One skilled in the art will recognize that, typically, an object includes myriad molecular components; however, for simplicity, FIG. 1 depicts object 118 having only two molecular components—object features 120-1 and 120-2, which are located at two different voxel locations.

During a measurement period, stage 108 moves object 118 along the x-direction such that it passes through modulated beam 114. As the object moves, object features 120-1 and 120-2 within object 118 act as point objects that scatter the radiation of primary beams 116-1 through 116-5, thereby giving rise to a plurality of scatter patterns, each of which is unique to each object feature. FIG. 1 depicts a snapshot in time in which the scatter pattern arising from object feature 120-1 includes scatter signal 122-1 and the scatter pattern arising from object feature 120-2 includes scatter signal 122-2.

Moving object 118 through modulated beam 114 via stage 108 represents only one means for changing the interaction between the first plurality of beam elements and the object in a time-dependent manner. Other means for changing this interaction include moving source 102 and/or detector 106 and/or coded aperture 104, changing the code of coded aperture 104, changing the energy spectrum and/or intensity of radiation fan 110 as a function of time, and varying the characteristics of modulated beam 114 by providing source 102 such that it is a multi-source array operative for varying its emitted radiation in a time-dependent manner.

Each of scatter signals 122-1 and 122-2 scatters at a Bragg scattering angle (relative to the direction of propagation of the fan beam incident on it), based on the energy of the incident beam and the molecular structure of the feature from which it scatters. For example, as depicted in FIG. 1, scatter signal 122-1 scatters from object feature 120-1 at angle θ1 relative to the direction of propagation of primary beam 116-2. In similar fashion, scatter signal 122-2 scatters from object feature 120-2 at angle θ2 relative to the direction of propagation of primary beam 116-4.

Due to the relative motion between the source and object, angles θ1 and θ2 change as a function of time. In addition, due to the structured illumination, each point in the object is illuminated several times from a variety of different incident angles during the measurement period. This multiplicity of illumination leads to an N-fold enhancement in the available scatter signal (where N is the number of times each voxel is illuminated), which can enable operation at lower incident photon flux and/or faster scanning of object 118. In addition, the angular diversity of the illumination combined with the known pattern of coded aperture 104 results in a scatter signal whose point of origin in space can be accurately determined. As a result, the identify of each material, f(q), at each object voxel can be readily deduced. Further, illuminating the object from a variety of angles mitigates some of the challenges associated with texturing and helps ensure an accurate measurement of the average molecular structure of object 118.

It should be noted that Bragg's law (Eq. 1) shows that both E and θ must be known in order to identify a measured x-ray with a particular value of q. While many prior-art approaches keep either E or θ fixed as the other parameter is scanned (e.g., angle- or energy-dispersive schemes), it is an aspect of the present invention that both E and θ are allowed to take on a variety of values.

It is yet another aspect of the present invention that scattered photons originating from different primary beams fall on the same detector elements. This multiplexing affords embodiments of the present invention with a highly-parallel measurement geometry in which the information content per source photon is high. As a result, embodiments of the present invention can scan large volumes in short times and have fewer required number of detector elements than prior-art imaging coherent scatter imaging systems.

Careful review of Eq. 1 reveals an inverse relationship between scatter angle and the energy of the scattered x-ray photon. In other words, small values of θ correspond to large values of E (and vice-versa). For an x-ray source with energy range [$E_{min}$, $E_{max}$], this results in a finite range of possible scatter angles for a given value of q. As a result, based on the bounds on the values of E and q, the optimal detector geometry to maximize the information obtained for a given constraint on the detector budget (e.g., total area, number of pixels, detector cost, etc.) can be determined. Further, as demonstrated below, exploitation of this relationship enables the present invention to distinguish between different materials located at different voxels within an object based on the time, position, and energy-dependence of the measured scattered photons.

It is another aspect of the present invention that direct measurement of the energy of the scattered radiation using an energy-sensitive detector facilitates this exploitation of the Bragg relationship. It should be noted that prior-art x-ray imaging systems typically employ energy-integrating detectors, where signals from interactions between an x-ray beam and materials are accumulated over an entire radiation spectrum. As a result, and in contrast to embodiments of the present invention, prior-art x-ray imaging systems are unable to discriminate between received radiation having different energies and, therefore, cannot use that knowledge to exploit Bragg's law. In addition, while one can make compressive measurements using a detector whose dimensionality is less than that of the object's being illuminated, energy-sensitivity is crucial to making non-compressive measurements of the full 4D (3 spatial+1 material) object.

As each of object features 120-1 and 120-2 approaches the x=0 plane, at which detector 106 is located, the magnitude of each of θ1 and θ2 decreases for detected scatter radiation and the energy of the scattered photons incident at detector 106 increases. The energy of the scattered photons eventually asymptotes when their corresponding object feature 120 is aligned with detector 106.

Figure 2:
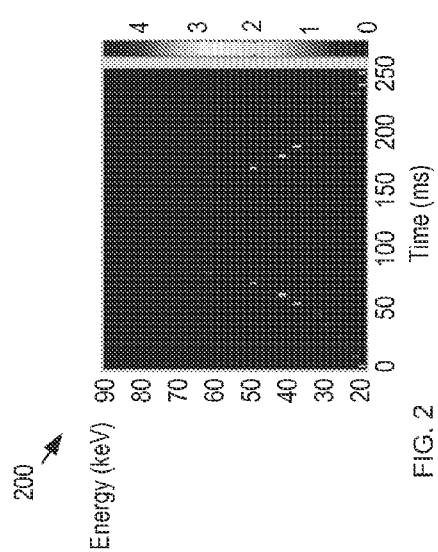
FIG. 2 depicts a plot of simulated raw data for scatter energy from an object feature 120 as a function of measurement time as the feature moves through modulated beam 114.

FIG. 2 depicts a plot of simulated raw data for scatter energy from an object feature 120 as a function of measurement time as the feature moves through modulated beam 114. Plot 200 is simulated based on a forward model of system 100 developed as follows.

Forward Model

A volumetric molecular image of object 118 can be estimated based on detected scatter signals 122 and a forward matrix, H, where, for a given measurement, g, and forward matrix H, an estimate of the object, $f_{est}$, is obtained by solving:

$$g = Hf + n \qquad (2)$$

where n corresponds to noise in system 100.

Forward matrix H is obtained by simulating system 100 by constructing a forward model relating $f(r_o,q)$ and measurement $g(E,t,r_d)$ spaces, where $f(r_o,q)$ is the position-dependent coherent structure function for object 118, $r_d$ is the position of detector 106 relative to source 102, and $r_o$ is the position of object 118.

Assuming the probability of an x-ray with energy E being scattered into a given solid angle can be given as:

$$p = \int \frac{d\sigma_{coh}(E)}{d\Omega} d\Omega, \text{ where } \frac{d\sigma_{coh}}{d\Omega} \propto L(\theta)f(r_o, q) \qquad (3)$$

is the coherent scatter cross section. L(θ) is a geometry-dependent term that takes into account the angular dependence of the scatter due to the factors independence of the coherent scatter effects. The measured number of x-rays at a given detector element for a point scatterer located at $(x_i, y_i, z_i)$ is therefore given as:

$$g(E, t, r_d) = \sum_{j,k} \delta\left(\frac{x_j z_o}{d} - [x_i - v_x t]\right) \delta\left(\frac{y_k z_o}{d} - [y_i - v_y t]\right) \times \qquad (4)$$

$$\delta(z - [z_i - v_z t]) \delta\left(E - \frac{hc q_o}{\sin[\theta_{jk}/2]}\right) L(\theta_{jk}) \phi(E),$$

where $\theta_{jk} = \theta(x_j z_o/d, y k z_o/d, z_o, r_d)$.

The forward model is then discretized by considering rectangular bins in the detector integration time and pixel size, and assuming a Gaussian energy response of the detector (which represents an approximation to the true response of an energy-sensitive detector) to yield:

$$g_{lmnp} \propto \sum_{j,k} dr_d L(\theta_{jk}) rect\left(\frac{\frac{[x_j z - x_i d]}{vd} - t_l}{\Delta t}\right) rect\left(\frac{\frac{[y_k z - y_i d]}{vd} - t_l}{\Delta t}\right) \times \qquad (5)$$

-continued $$rect\left(\frac{x_d - x_m}{\Delta x}\right) rect\left(\frac{y_d - y_n}{\Delta y}\right) \exp\left[-\left(\frac{\frac{hcq}{\sin\left(\frac{\theta_{jk}}{2}\right)} - E_n}{\Delta E}\right)^2\right],$$

where Δx, Δy, Δt, and ΔE are the effective detector element widths, integration time, and energy resolution, respectively.

The forward matrix, H, is obtained by evaluating $g_{lmnp}$ for a range of different input point objects. Additional details regarding forward-model development are disclosed by Greenberg, et al., in "Structured Illumination for Tomographic X-ray Diffraction Imaging," Analyst, Vol. 139, pp. 709-713 (2014), which is incorporated herein by reference.

As object 118 moves along the x-direction, object features 120-1 and 120-2 pass through and between the structured illumination of modulated beam 114. Detector 106, however, only records a signal when an object features is illuminated by x-rays and when the scatter angle is physically allowed by Eq. 1 above. As a result, plot 200 is curve E(t), which has a temporal modulation that uniquely identifies both the object's composition and location.

It should be noted that, since detector 106 is a single pixel having energy sensitivity, multiple, temporally-resolved measurements are acquired. As a result, the measurement is two dimensional (i.e. 1 temporal dimension+1 energy dimension) and the approach of the present invention can be considered to be compressive in the sense that the object embedding dimension exceeds the measurement dimension.

Figure 3:
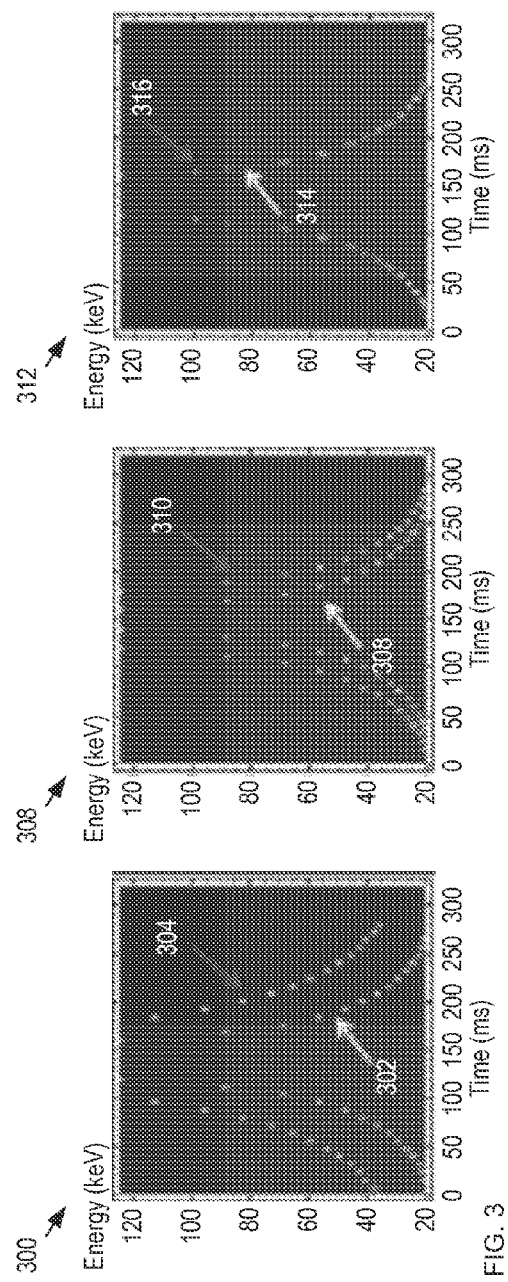
FIG. 3 depicts plots of simulations of raw signals for an object having two substantially identical object features corresponding to different conditions.

FIG. 3 depicts plots of simulations of raw signals for an object having two substantially identical object features corresponding to different conditions. The simulations depicted in plots 300, 306, and 312 are developed using the forward model described above. Insight into how three-dimensional object information is encoded in two-dimensional measurement data by comparing the E(t) curves shown in plots 300, 306, and 312, which demonstrate how slight changes in the target object manifest as changes in the detected energy versus time.

Plot 300 includes traces 302 and 304, which depict raw signals obtained from object features 120-1 and 120-2, respectively, when the object features consist of different materials (i.e., they have different q) but are substantially co-located. Traces 302 and 304 show that different materials yield E(t) curves having different slopes.

Plot 306 includes traces 308 and 310, which depict raw signals obtained from object features 120-1 and 120-2 that consist of the same material but have different initial positions along the x-direction. It can be seen from traces 308 and 310 that different initial locations manifest as E(t) curves that are identical in shape but that are shifted relative to one another in time.

Plot 312 includes traces 314 and 316, which depict raw signals obtained from object features 120-1 and 120-2 that consist of the same material but are at different ranges (i.e., have different positions along the z-direction). It can be seen from traces 314 and 316 that different ranges manifest as E(t) curves that which yield E(t) curves that exhibit temporal modulation indicative of the point of origin of the scatter signal (as objects at different z positions yield curves with the same structure but different frequencies).

One skilled in the art will recognize, after reading this Specification, that plots 300, 306, and 312 provide the three distinct pieces of information required to describe the curve E(t) (namely slope, temporal modulation, and time at which the asymptote occurs) are sufficient to fully describe object 118. It should be noted that, in contrast to the prior art, no detector-side code is required to disambiguate this signal.

Figure 4A:
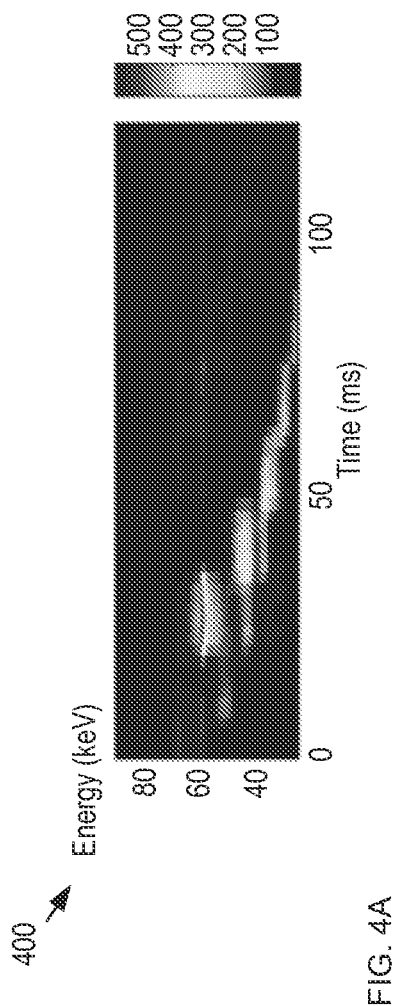
FIGS. 4A-B depict simulated and experimentally measured data, respectively, for system 100.
Figure 4B:
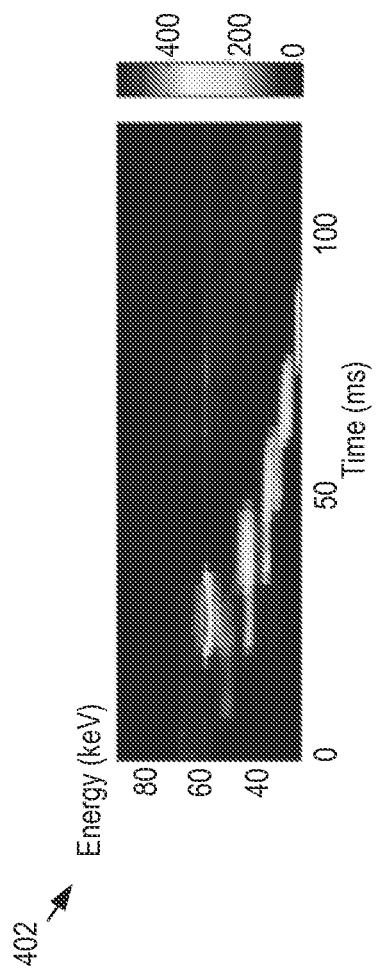

FIGS. 4A-B depict simulated and experimentally measured data, respectively, for system 100. Plots 400 and 402 depict data for a sample comprising a 6×14 mm vial of graphite powder, where the sample is moved linearly along the x-direction in 0.5 mm steps and where, at each step, a source current of 25 mA is applied for 4 sec.

Plot 400 shows simulated data generated using the forward model described above.

Plot 402 shows experimental data obtained using system 100, wherein source 102 is a 125 keV tungsten-anode x-ray tube and coded aperture 104 is a 3-mm thick lead sheet having an array of pinhole apertures with a diameter of approximately 1.5 mm on a pitch of approximately 3 mm, and wherein detector 106 is a single-pixel energy-sensitive x-ray radiation detector located x=0 and at a z distance of 998 mm from source 102.

Plots 400 and 402 show the expected E(t) trend along with appropriate modulation due to the coded-aperture pattern. In contrast to the well-separated curve shown above in FIG. 2, the finite extent of the object gives rise to a continuum of curves along the temporal direction, while the finite detector energy resolution results in blurring along the energy dimension. Taking these effects into account, however, plots 400 and 402 show that there is good agreement between the forward model and experimental results.

As discussed briefly above, an estimated volumetric molecular image of an object, $f_{est}(x,z,q)$, can be developed based on the detected scatter radiation and the forward model described above.

Figures 5A, 5B:
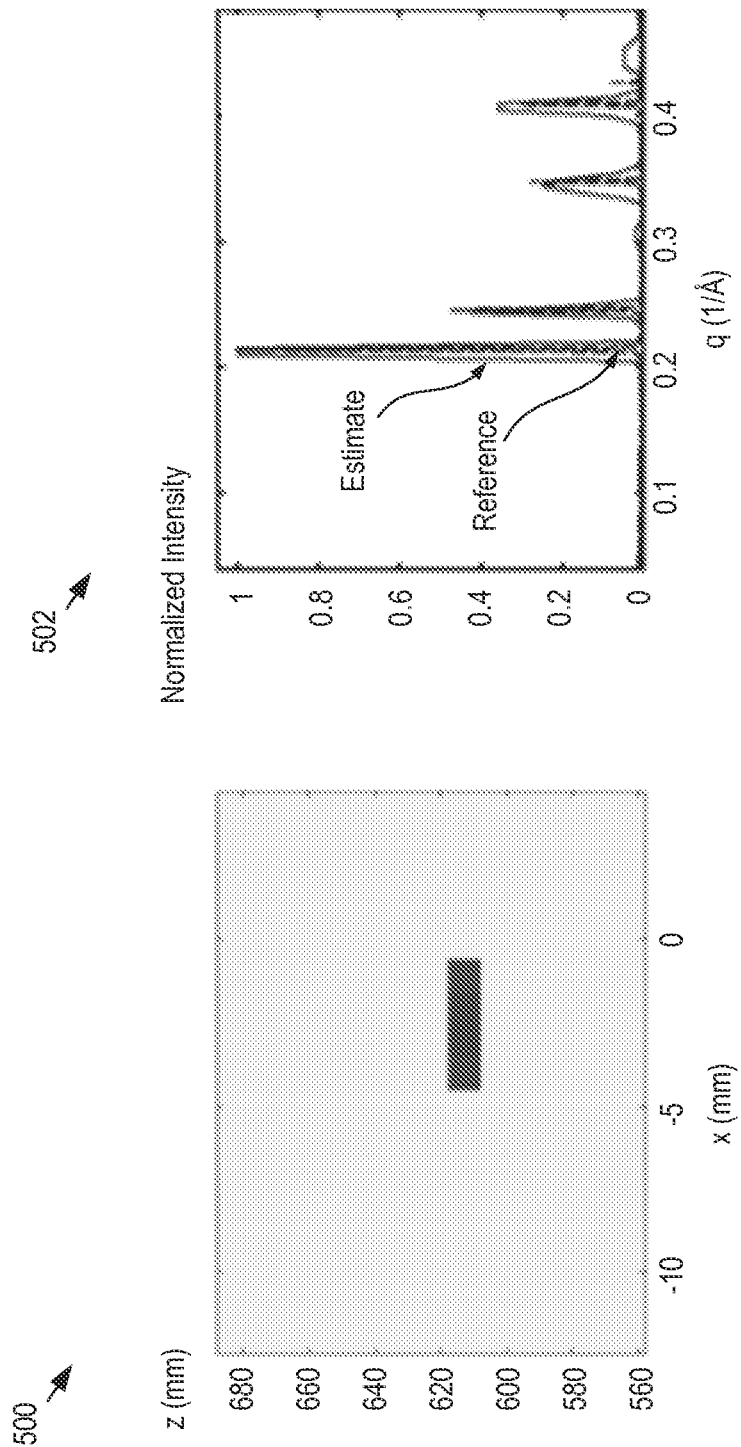
FIGS. 5A-B depict an estimated object, $f_{est}$, projected onto the spatial and momentum transfer axes, respectively.

FIGS. 5A-B depict an estimated object, $f_{est}$, projected onto the spatial and momentum transfer axes, respectively. For plots 500 and 502, $f_{est}(x,z,q)$ is calculated using the measured data, the modeled H, and a maximum likelihood estimation (MLE) reconstruction algorithm. It should be noted that other reconstruction algorithms, such as Poisson MLE, can be used without departing from the scope of the present invention.

Plot 500 shows a spatial map of estimated object 118, where the map is obtained by summing over all q at each position.

Plot 502 depicts a momentum transfer spectrum at z=613 mm for several different values of $x_i$.

It should be noted that, while system 100 is in accordance with the present invention, it is often preferable to image an object via a higher dimensionality system.

Having provided a simplified overview of the fundamental principles of coherent-scatter imaging using structured illumination, an illustrative embodiment of the invention is now presented.

Figure 6:
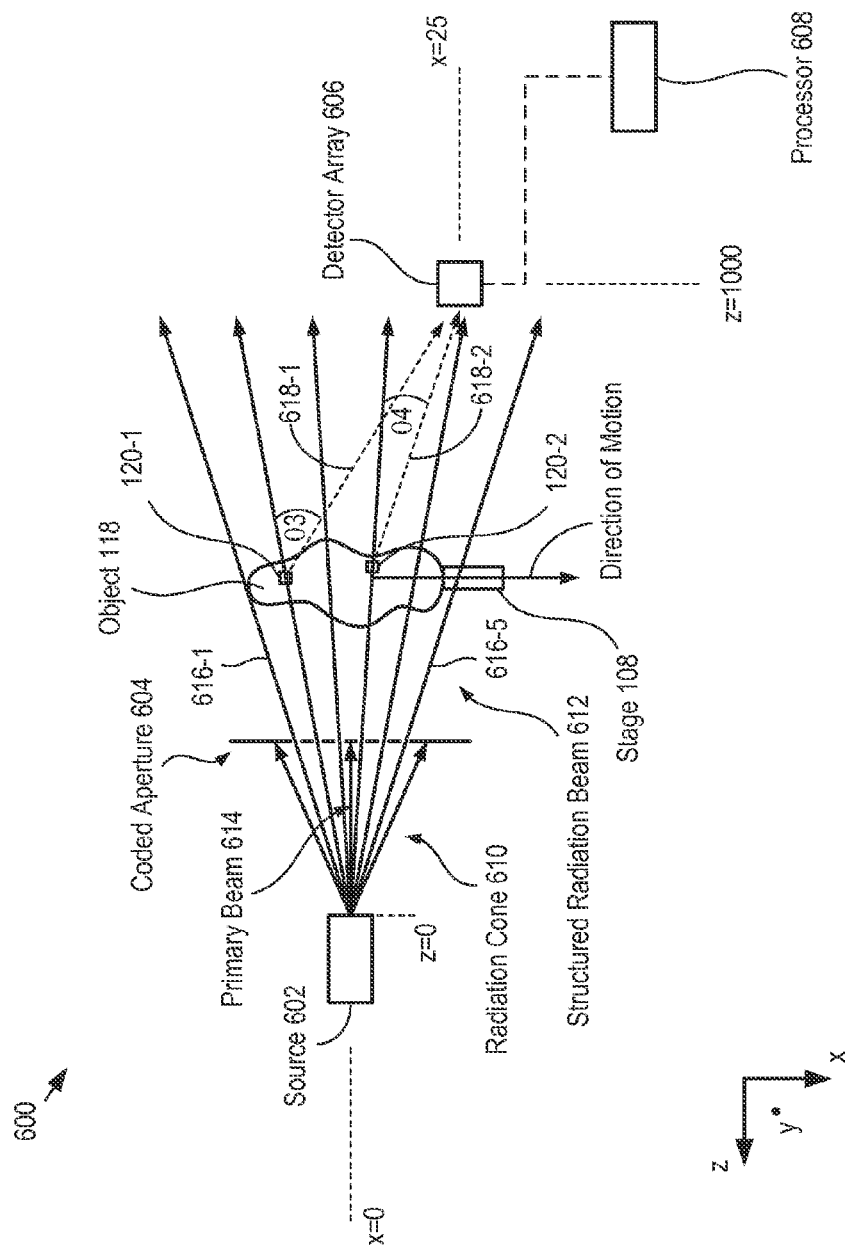
FIG. 6 depicts a schematic diagram of a portion of a molecular imaging system in accordance with an illustrative embodiment of the present invention.

FIG. 6 depicts a schematic diagram of a portion of a molecular imaging system in accordance with an illustrative embodiment of the present invention. System 600 includes source 602, coded aperture 604, stage 108, detector array 606, and processor 608.

Figure 7:
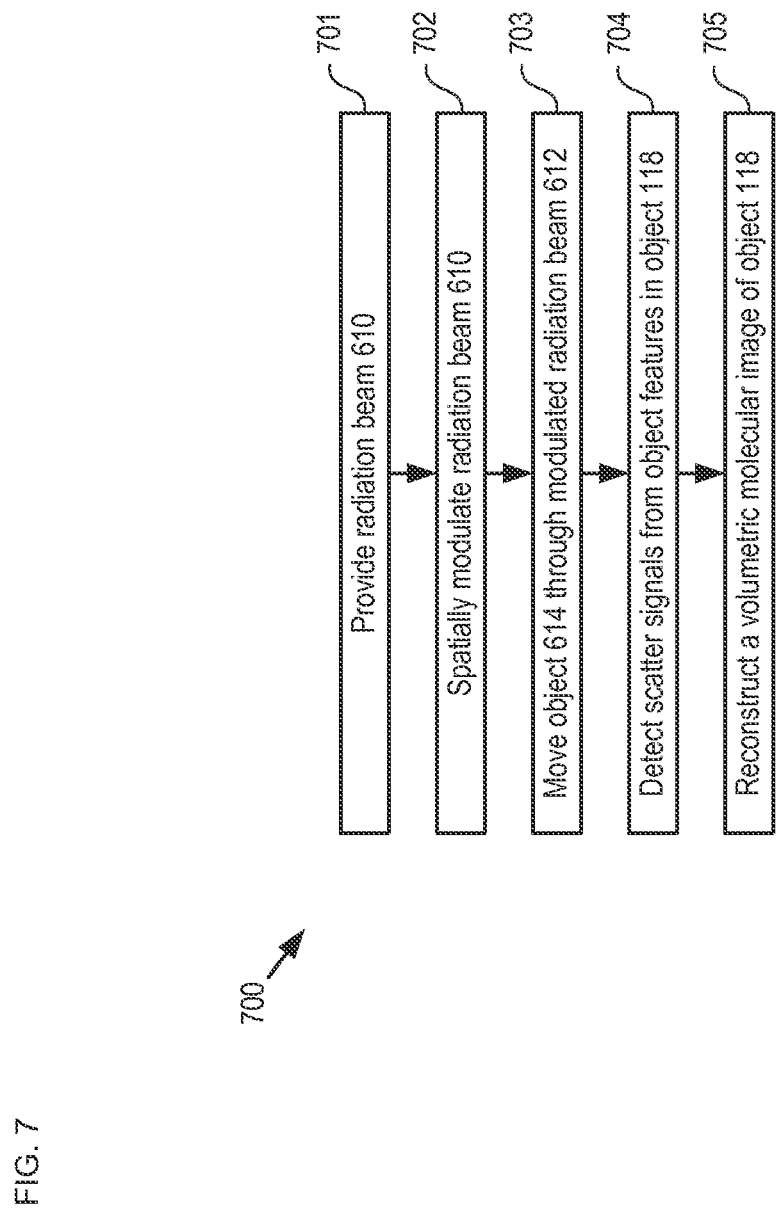
FIG. 7 depicts operations of a method suitable for estimating the structural and molecular composition of an object in accordance with the illustrative embodiment of the present invention.

FIG. 7 depicts operations of a method suitable for estimating the structural and molecular composition of an object in accordance with the illustrative embodiment of the present invention. Method 700 is described with continuing reference to FIG. 6, as well as reference to FIGS. 8-9. Method 700 begins with operation 701, wherein source 602 provides radiation cone 610.

Source 602 is a conventional x-ray an x-ray tube operated at 175 keV and 5 mAs. It has an opening angle of 30×40 degrees, thereby providing radiation cone 610 as a substantially cone-shaped beam of polychromatic x-ray radiation. It will be clear to one skilled in the art, however, after reading this Specification, how to specify, make, and use embodiments of the present invention comprising alternative x-ray radiation sources.

It should be noted that prior-art coherent-scatter imaging schemes require an x-ray source that is filtered either spectrally (to a quasi-monochromatic distribution) or spatially to produce an invertible signal. Unfortunately, this filtering has the unfortunate consequence that a large fraction of x-rays emitted from the source are blocked and do not interact with the object to contribute to a measurable signal. As a result, prior-art approaches require either a prohibitively bright x-ray sources or long scan times. The effect is exacerbated by the fact that the coherent scatter signal is intrinsically dim as compared to the central beam (i.e., the x-ray beam at the center of radiation cone 610).

It is an aspect of the present invention, however, that the x-ray radiation used to interrogate an object is filtered minimally both spatially and spectrally. As a result, the x-ray photons in radiation cone 610 are better utilized than in the prior art. This enables embodiments of the present invention to realize real-time imaging while keeping the power level of the x-ray source at an acceptable level and enabling the use of standard x-ray tubes.

At operation 702, coded aperture 604 spatially modulates radiation cone 610 to form structured radiation beam 612.

Figure 8:
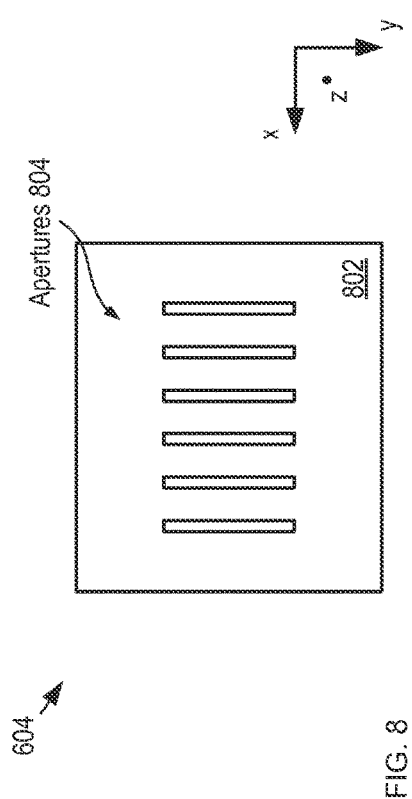
FIG. 8 depicts a schematic drawing of a coded aperture in accordance with the illustrative embodiment of the present invention.

FIG. 8 depicts a schematic drawing of a coded aperture in accordance with the illustrative embodiment of the present invention. Coded aperture 604 comprises plate 802 and a linear array of apertures 804 arranged along the y-dimension.

Plate 802 is a suitable rigid plate of material suitable for blocking x-ray photons in radiation cone 610. An exemplary plate 802 is a lead sheet having a thickness of approximately 3 mm, although one of skill in the art will recognize that there are many equivalent materials and/or thicknesses.

Each of apertures 804 is a linear opening (i.e., slit) formed through plate 802 having a width (in the x-dimension) of approximately 1 mm and a height (in the y-dimension) within the range of approximately 10 mm to approximately 40 mm. Apertures 804 are arranged in an linear array of five elements having a period of 8 mm. In some embodiments, the period of apertures 804 is within the range of approximately 2 mm to approximately 10 mm. One skilled in the art will recognize that the shape, dimensions, and spacing of features 804 are matters of design choice and will depend upon several factors, including desired system performance, detector sensitivity and design, overall system design, etc. It should also be noted that, although the array of apertures 804 is a linear array of five elements, coded aperture 604 can include any number and/or arrangement of features without departing from the scope of the present invention.

Like coded aperture 104 described above, coded aperture 604 introduces a position-dependent modulation of the radiation used to interrogate an object. In addition, coded aperture 604 is positioned relative to source 602 such that the coded aperture removes central beam 614 from structured radiation beam 612. Removal of central beam 614 enables measurement of the relatively weak scatter signal and conditions the inherently-multiplexed scatter signal such that one can invert (de-multiplex) the measured signal to recover the object properties, as discussed below. Coded aperture 604, therefore: (1) acts to effectively reduce the required detector dimensionality; (2) enables the use of a large fraction of the full polychromatic cone beam for molecular imaging; and (3) substantially minimizes the required detector coverage.

Coded aperture 604 and source 602 collectively provide structured radiation beam 612 as a linear array of five beam elements, each of which is a fan beam (i.e., fan beams 616-1 through fan beam 616-5). Fan beams 616-1 through fan beam 616-5 are arrayed along the x-direction such that the long axis of each fan beam is oriented along the y-direction. Although the illustrative embodiment includes a coded aperture that gives rise to a structured radiation beam having five beam elements, it will be clear to one skilled in the art, after reading this Specification, how to specify, make, and use alternative embodiments of the present invention that interrogates an object with a structured radiation beam having any practical number of beam elements, each of which can have any suitable shape.

At operation 703, for a measurement period of time t(0) through time t(1), stage 108 translates object 118 along a direction of motion that is aligned with the x-direction such that each of fan beams 616-1 through 616-5 interrogates the object during the measurement period.

Stage 108 is a conventional single-axis linear translation stage. Stage 108 moves object 118 with an object velocity of approximately 250 mm/sec. It should be noted that this object velocity is merely exemplary and that any object velocity suitable for enabling measurement of the molecular structure of the object with satisfactory resolution, based on the temporal integration time of system 600 (as discussed below), is within the scope of the present invention.

In some embodiments, stage 108 is other than a linear stage and moves object 118 with a motion that is other than strictly linear, such as rotational, or both rotational and translational.

As discussed above and with respect to FIG. 1, moving an object under test through a modulated radiation beam via a stage represents only one means for changing the interaction between the first plurality of beam elements and the object in a time-dependent manner. Other means for changing this interaction include moving source 602 and/or detector array 606 and/or coded aperture 604, changing the code of coded aperture 604, changing the energy spectrum and/or intensity of radiation cone 610 as a function of time, and varying the characteristics of structured radiation 612 by providing source 602 such that it is a multi-source array operative for varying its emitted radiation in a time-dependent manner.

As object 118 travels through the different fan beams of structured radiation beam 612, features 120-1 and 120-2, contained within the volume of the object, give rise to scattered radiation, as discussed above. FIG. 6 depicts system 600 at a point in time at which the scattered radiation includes scatter signals 618-1 and 618-2. Each of scatter signals 618-1 and 618-2 scatters at a Bragg scattering angle to the direction of propagation of the fan beam incident on it, wherein the scattering angle is based on the energy of the incident beam and the molecular structure of the feature from which it scatters. For example, as depicted in FIG. 6, scatter signal 618-1 scatters from feature 120-1 at angle θ3 relative to the direction of propagation of incident fan beam 616-2. In similar fashion, scatter signal 618-2 scatters from feature 120-2 at angle θ4 relative to the direction of propagation of incident fan beam 616-4.

At operation 704, detector array 606 detects scatter radiation from object features within object 118.

Figure 9:
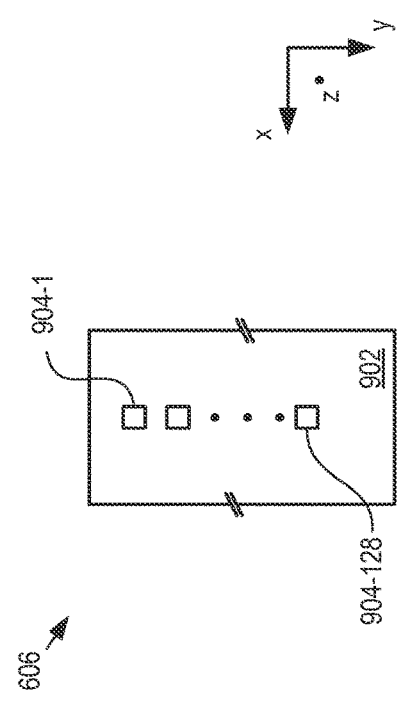
FIG. 9 depicts a schematic drawing of a detector array in accordance with the illustrative embodiment of the present invention.

FIG. 9 depicts a schematic drawing of a detector array in accordance with the illustrative embodiment of the present invention. Detector array 606 includes substrate 902 and detector elements 904-1 through 904-128. In the exemplary system depicted in FIG. 9, detector array 606 is located at x=25 and z=1000 mm.

Detector elements 904-1 through 904-128 (referred to, collectively, as detector elements 904) are monolithically integrated on substrate 902 in conventional fashion. Each of detector elements 904 is an energy-sensitive detector having a square detector region of 0.8 mm per side and having 64 energy channels. Detector elements 904 are arranged in a linear array oriented along the y-axis with a spacing of approximately 3.5 mm. Although detector elements 904 are arranged along a direction that is orthogonal with the direction of motion of object 118, in some embodiments the detector elements are aligned along a direction that is aligned with the direction of motion of the object.

As noted above, the use of energy-sensitive detector elements enables direct measurement of the energy of the scattered radiation, thereby facilitating the exploitation of the Bragg relationship provided in Eq. (1). This is in contrast to prior-art x-ray imaging systems that employ energy-integrating detectors that cannot discriminate between the energy of x-ray photons received from anywhere within a broad radiation spectrum.

It should be noted that the characteristics and layout of the detector elements play a large role in the performance of embodiments of the present invention. The key characteristics of an individual detector element are its temporal and energy resolution, size, and quantum efficiency. In order to ensure suitable performance, the temporal resolution and pixel size should be chosen such that they, in conjunction with the coded aperture, yield a desired spatial resolution. The required energy resolution can then be determined so that its contribution to the uncertainty of the momentum transfer at each voxel is less than that due to the angular uncertainty. In many cases, the choice of detector material, size, spectroscopic performance, and quantum efficiency are interrelated, and should be therefore carefully optimized for a particular application. Nevertheless, mm-scale spatial resolution can be achieved with ~0.1 $nm^{-1}$ momentum-transfer resolution over a range of object locations using readily available detectors with a pixel size of approximately 1 mm, an energy resolution of a few keV, and a temporal resolution of approximately 1 millisecond. While the characteristics of the detector pixels are important, however, it should be noted that the performance of system 600, as a whole, is strongly dependent upon the location of the detector pixels.

In some embodiments, at least some of detector elements 904 are energy-integrating detector elements. In some embodiments, at least some of detector elements 904 are oriented in different planes (e.g., different z-planes or along the x- or y-planes). Orienting detector elements in different planes can improve signal conditioning for better quality images, as well as enable the collection of more scatter photons per unit time for increased signal levels and/or faster scan rates.

In some embodiments, detector elements 904 are arranged in a linear array aligned with the direction of motion of object 118. In some embodiments, detector elements 904 are arranged in an arrangement other than a regular linear array. In some embodiments, detector array 606 includes more or less than one hundred and twenty-eight detectors and, as described above and with respect to FIG. 1, in some embodiments, can include only a single detector element. It should be noted, however, that while volumetric molecular imaging can be realized using a single detector element, the use of multiple detector elements typically affords improved performance. It can be shown, for example, that mean-squared error (mse) is reduced and higher-fidelity reconstructions are possible when either or both of the mean photon number or the number of detector elements is increased. It is worth nothing, however, that not all detector locations are equally useful. Because coherent scatter tends to be limited to a small angular range, detector elements clustered closer to the primary beams (e.g., primary beams 116, fan beams 116, etc.) tend to yield higher information content than those located at large scatter angles.

It should be further noted that, while a single linear array of detector elements is sufficient to reconstruct the entire volume of object 118, the addition of more detector elements can afford embodiments of the present invention further advantages over the prior art. For example, adding more pixels enables more information to be measured at fixed mAs in at least two ways. First, it simply enables more total signal to be acquired, which improves signal-to-noise ratio (SNR) (even if the information in the signals is redundant). Second, it increases measurement diversity, which can improve the conditioning of the system.

While the imaging performance almost always benefits from the addition of detectors, the constraints imposed by cost, size, and data management often impose limits on the practical detector budget. It is important, therefore, to optimize the imaging performance for a fixed number of detector pixels.

Figure 10:
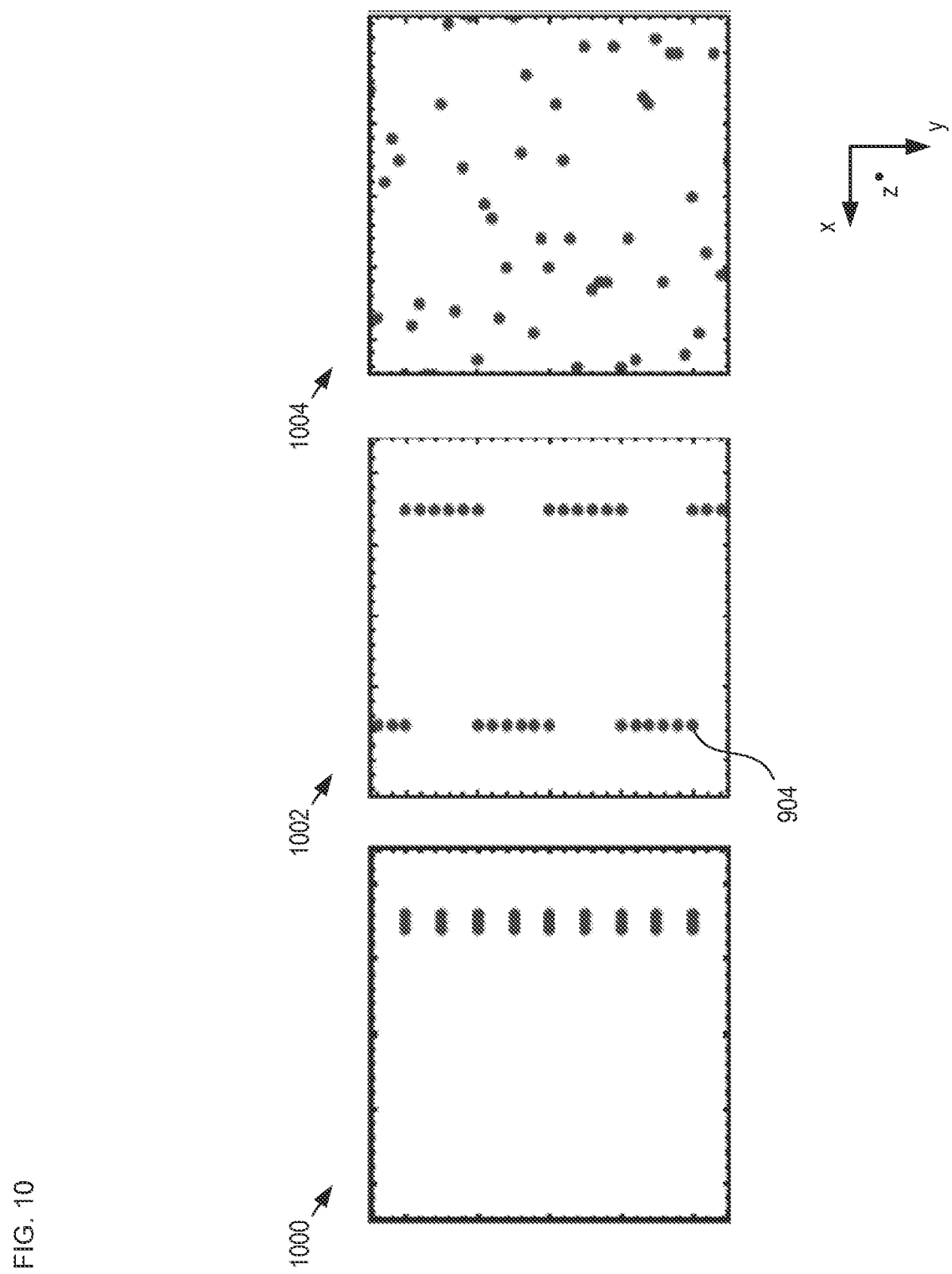
FIG. 10 depicts schematic drawings of exemplary alternative arrangements of detector elements in accordance with the present invention.

FIG. 10 depicts schematic drawings of exemplary alternative arrangements of detector elements in accordance with the present invention. In the figure, each circle indicates the center of a detector element 904.

Detector array 1000 is a two-dimensional array of detector elements 904 centered at the same location as in detector array 902. In detector array 1000, however, the detector elements have an increased pixel pitch along the y-direction such that the number of pixels is fixed. Typically, the performance of system 600 using detector array 1000 is nearly identical to that using detector array 606.

Detector array 1002 is a two-dimensional array of detector elements 904, where the detector elements are arranged in two broken, non-overlapping linear arrays with pixel pitch being the same as for detector array 606. In the limit that the pixel pitch is still sufficiently small that all object voxels are able to scatter to the detector, the performance of system 600 using detector array 1000 can provide significant improvement in reconstruction fidelity at low mAs as compared to the performance of system 600 using detector array 606.

Detector array 1004 is a two-dimensional array of detector elements 904, where the detector elements are arranged in a random arrangement. It can be shown that system performance using detector array 1004 is comparable to that using detector array 1002.

Returning now to system 600, as object 118 passes through the fan beams 616, the motion of object 118 and the spatial modulation of coded aperture 604 impart a time dependency on each of scatter beams 620-1 and 620-2 and the intensity of the scattered x-rays at different energies and positions are recorded at detector array 606 as a function of time. It should be noted that each object voxel is illuminated several times from a variety of different incident angles during the measurement time period. As discussed above, the multiplicity of illumination leads to an N-fold enhancement in the available scatter signal (where N is the number of times each voxel is illuminated), which can enable operation at lower incident photon flux and/or faster scanning of object 118. In addition, the angular diversity of the illumination combined with the known pattern of coded aperture 604 results in a scatter signal whose point of origin in space can be accurately determined. As a result, the identity of each material, f(q), at each object voxel can be readily deduced.

Figure 11:
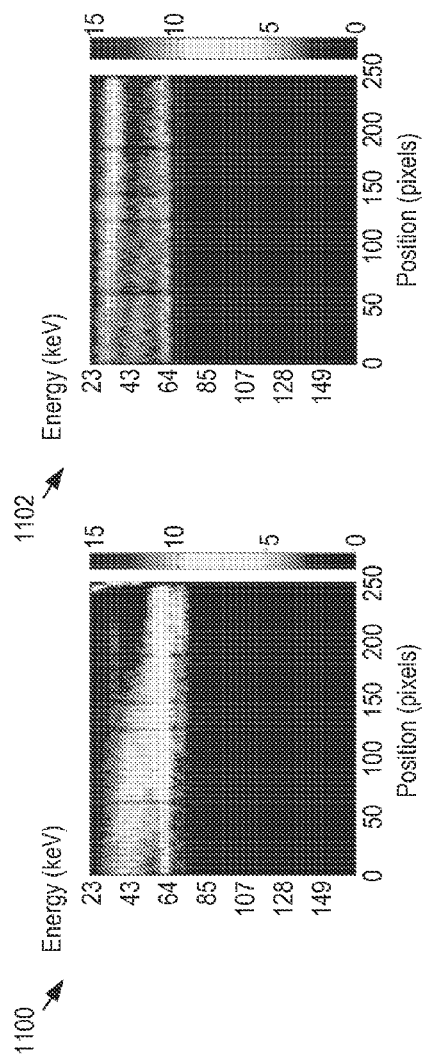
FIG. 11 depicts raw data from a scan of a sample at two different times within the measurement period.

FIG. 11 depicts raw data from a scan of a sample at two different times within the measurement period. Plots 1100 and 1102 depict the scatter radiation detected from object 118 comprising a cylindrical vial of aluminum powder (oriented with its long axis along the y-direction) at times when the scatter angle is small and large, respectively. The plots demonstrate the proportional dependence of E and 1/x as predicted by Eq. 1 above. It can be seen that, as object 118 moves, the shape of the curve in E-x space changes because the relative scatter angle between the object and any given detector element changes.

At operation 705, processor 608 reconstructs a volumetric molecular image of object 118.

The present invention enables two otherwise identical objects placed at different initial x-locations ($x_i$) to be distinguished, since they will yield the same scatter signal with a relative temporal shift. Similarly, identical objects at different positions along the z-direction result in scatter signals with different temporal modulations as well as, potentially, different spatio-spectral signatures. In general, intelligent design of coded aperture 604 and placement of detector elements 904 enable unique identification of the material composition of three-dimensional object 118.

In some embodiments, the fact that each object voxel is illuminated multiple times during a measurement is exploited by adapting the measurement process during the measurement period. Because some information is obtained from each object voxel at multiple points throughout a single scan, the information obtained in previous measurements of the scan can be used to inform subsequent measurements. As a result, in some embodiments, at least one of the following is varied in an object-dependent way to improve system performance under a given set of constraints (e.g., a fixed source power or dose budget, scan time, or available detector coverage):

i. rate of the object motion; or
  ii. direction of object motion; or
  iii. coded-aperture pattern; or
  iv. source properties to yield the optimal image; or
  v. any combination of i, ii, iii, and iv.

Adapting the code of the coded aperture, in particular, can afford embodiments of the present invention with additional advantages over the prior art by employing a series of codes that complement each other to offset tradeoffs between imaging performance metrics. For example, a high-transparency code with poor conditioning might be used first to provide a rough estimate of the total scatter brightness or focus primarily on a particular spatial scale of interest. Afterward, a lower-transparency code with better conditioning could be used to resolve finer features of the object. Furthermore, an ability to choose code structure "on the fly" (e.g., using a "programmable liquid element"), could substantially maximize the amount of information obtained about an object in the fewest number of measurements on an object-by-object basis, thereby leading to shorter scan times and/or lower radiation doses.

As noted above, in some embodiments it is desirable to provide structured radiation beam 612 such that it includes a pattern of beam elements having more or less than five elements, and/or where at least one beam element is not a fan beam. As discussed above, a fundamental role of the code of coded aperture 604 is to make the scatter signal originating from each object voxel as different as possible—in other words, to condition the scatter radiation signal for inversion.

The best choice of code design does not hinge solely on the ability to distinguish the signal from different object voxels, however. For example, creating an adequately modulated code necessarily means blocking some of the incident source flux. At the same time, many x-ray diffraction imaging approaches are photon-starved, which argues in favor of having a mostly open mask with sparse modulation. As a result, in some cases, the design of coded aperture 604 will depend on many factors, including the application for system 600 is intended, required image resolution, desired imaging speed, cost, manufacturability, and the like.

Figure 12:
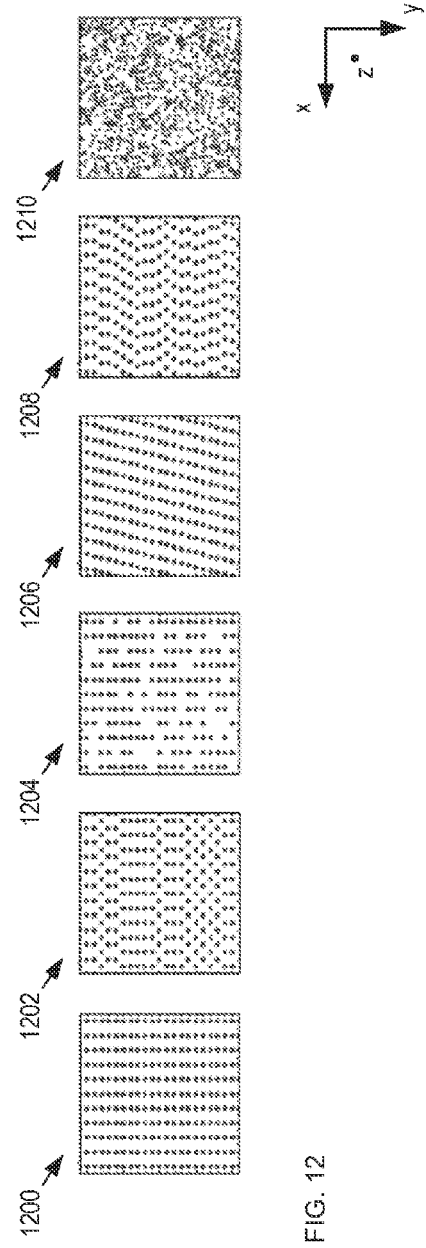
FIG. 12 depicts schematic drawings of examples of alternative coded apertures suitable for use in the present invention.

FIG. 12 depicts schematic drawings of examples of alternative coded apertures suitable for use in the present invention. One skilled in the art will recognize, after reading this Specification, that coded apertures 1200 through 1210 represent only a fraction of myriad code designs that are possible without departing from the scope of the present invention.

Coded aperture 1200 includes a code comprising a two-dimensional array of pinholes, where the array is periodic along the x-direction (i.e., in the direction of motion of object 118)—a simple instantiation of a code that provides range information. This simple harmonic code produces a sequence of fan beams that is completely unstructured along the y-direction, however. Distinction of signals originating from different y locations in object 118, therefore, relies upon the layout and spatial resolution provided by the detector elements 1204.

Coded aperture 1202 improves upon the code of coded aperture 1200 by implementing random π phase changes along the y-direction, which provides modulation in both the x- and y-directions. As a result, scatter signals originating at different values of y are more readily distinguished.

Coded aperture 1204 is an arrangement of pinhole apertures that includes randomly blocked features.

Coded aperture 1206 is an arrangement of pinhole apertures having a linearly varying phase along the y-direction.

Coded aperture 1208 is an arrangement of pinhole apertures having a randomly varying phase along the y-direction.

Coded aperture 1210 includes a code having a random two-dimensional distribution of pinhole apertures.

In general, it is expected that more highly structured codes are likely to give better results at large mAs (where photon noise is negligible), while codes with higher transmission are likely to achieve smaller mse at low mAs, with a transition point at approximately $10^{-1}$ mAs (per integration time). In other words, coded apertures having high transmission outperform coded apertures with low transmission below $10^{-1}$ mAs, whereas the trend reverses above $10^{-1}$ mAs.

In some embodiments, coded aperture 604 includes a code that accentuates differences between adjacent object points but is still fairly open and has features whose sizes are matched to the targeted resolution.

While the use of a coded aperture that modulates radiation cone 610 along the direction of relative motion enables range information, in some embodiments, coded aperture 604 includes a code that is orthogonal in translation (e.g., a Hadamard or MURA pattern) to improve the imaging resolution along the cross-range dimension. This geometry enables fast, full-object imaging while requiring a reduced number of detector elements. It should be noted, however, that these results depend strongly on the properties of the detector, code structure, and the object (both its location and material composition).

Figure 13:
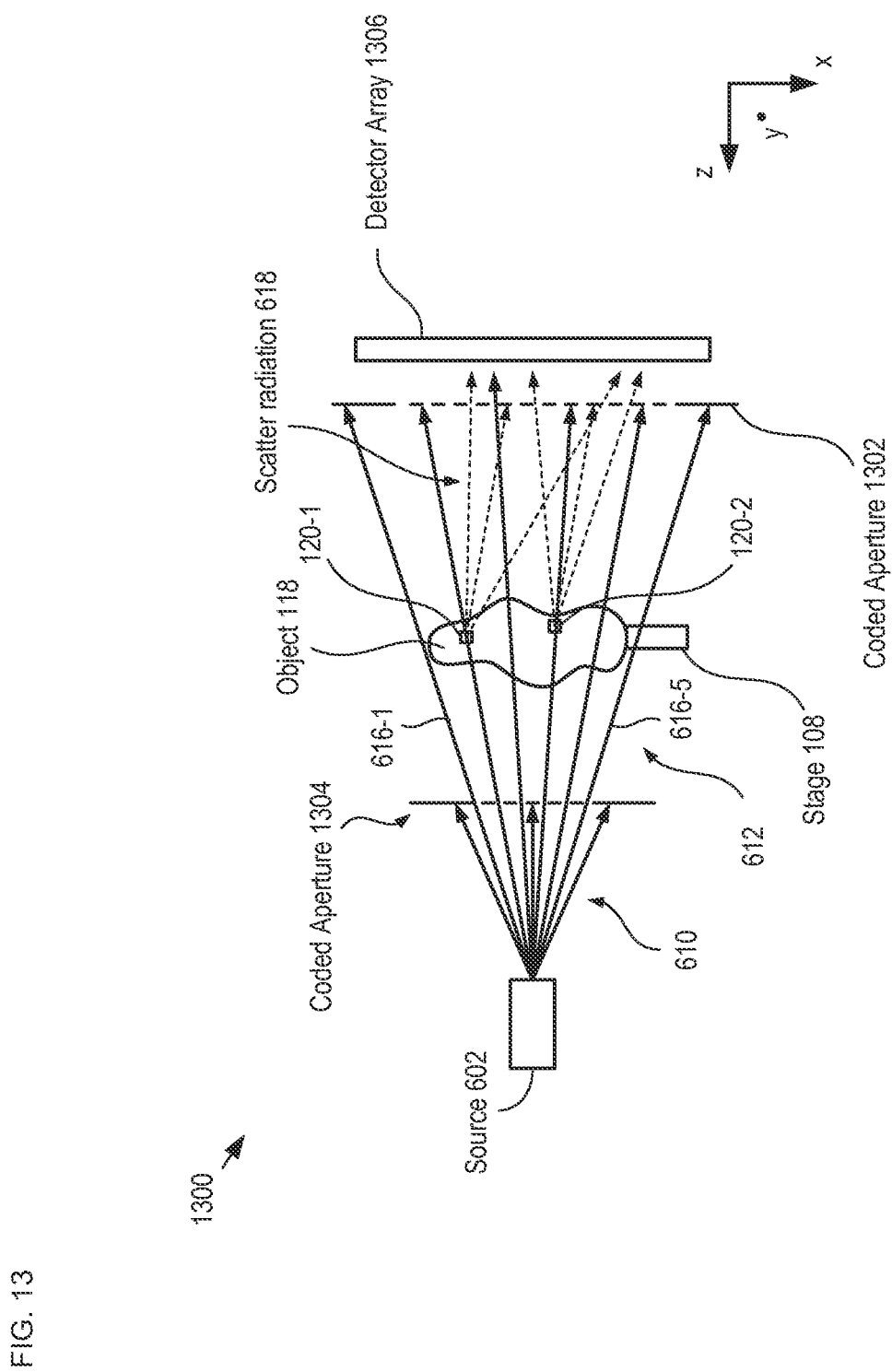
FIG. 13 depicts a schematic drawing of a molecular imaging system in accordance with a first alternative embodiment of the present invention.

FIG. 13 depicts a schematic drawing of a molecular imaging system in accordance with a first alternative embodiment of the present invention. System 1300 is a molecular imaging system that combines the principles of coherent scatter imaging using structured illumination with snapshot imaging techniques known in the prior art, such as is disclosed in U.S. patent application Ser. No. 14/350,073 entitled "Apparatus for Coded-Aperture x-ray Scatter Imaging and Method Therefor" and PCT Application PCT/US2014/014087 entitled "System for Improved Compressive Tomography and Method Therefor," each of which is incorporated herein by reference. System 1300 includes source 602, coded aperture 604, stage 108, processor 608, coded aperture 1302, and detector array 1304. In the example depicted here, coded aperture 1302 functions as a periodic range mask, while the inclusion of coded aperture 604 enables better system performance.

System 1300 includes coded aperture 1302 as a second coded aperture located between the object and the detector array to structure the scattered radiation. This second coded aperture enables acquisition of a volumetric scatter image from each beam element 616 in structured radiation beam 612 rather than requiring the object to pass through the full illumination structure. While this results in some blocking of photons by the second coded aperture, the improved conditioning obtained by combining many separate images of the same object voxels can lead to improved imaging resolution.

It should be noted that the inclusion of a second coded aperture gives rise to the modified forward model:

$$g(E, t, r_d) = \int dx dy dz dq L(\theta) f(x, z, y, q) \tag{6}$$
$$\Phi(E, z, y, z) t(x, y, z, r_d, E) \delta \left[ E - hcq \Big/ \sin\left(\frac{\theta}{2}\right) \right],$$

where $t(x,y,z,r_c,E)$ is the transmission function describing the energy-dependent and position-dependent detector-side coded aperture.

Each of coded apertures 1302 and 1304 is analogous to coded aperture 604.

Detector array 1306 is typically an array of detector elements, as described above.

The design of coded aperture 1302 depends on the design of coded aperture 1304 (and vice versa). For exemplary purposes, the design of coded aperture 1302 includes a periodicity along the y-direction.

In this configuration, the detector-side coded aperture (i.e., coded aperture 1302) modulates the scattered x-rays (i.e., scatter radiation 618) and yields information about the location of object 118 in the z-direction. This information augments the information regarding object range derived from the temporal structure of the signal (as described above); therefore, the code structure of coded aperture 1304 can be more open than the code structures described above and with respect to system 600. As a result, more radiation is received at detector array 1306, which can produce increased signal and improved SNR.

Figure 14:
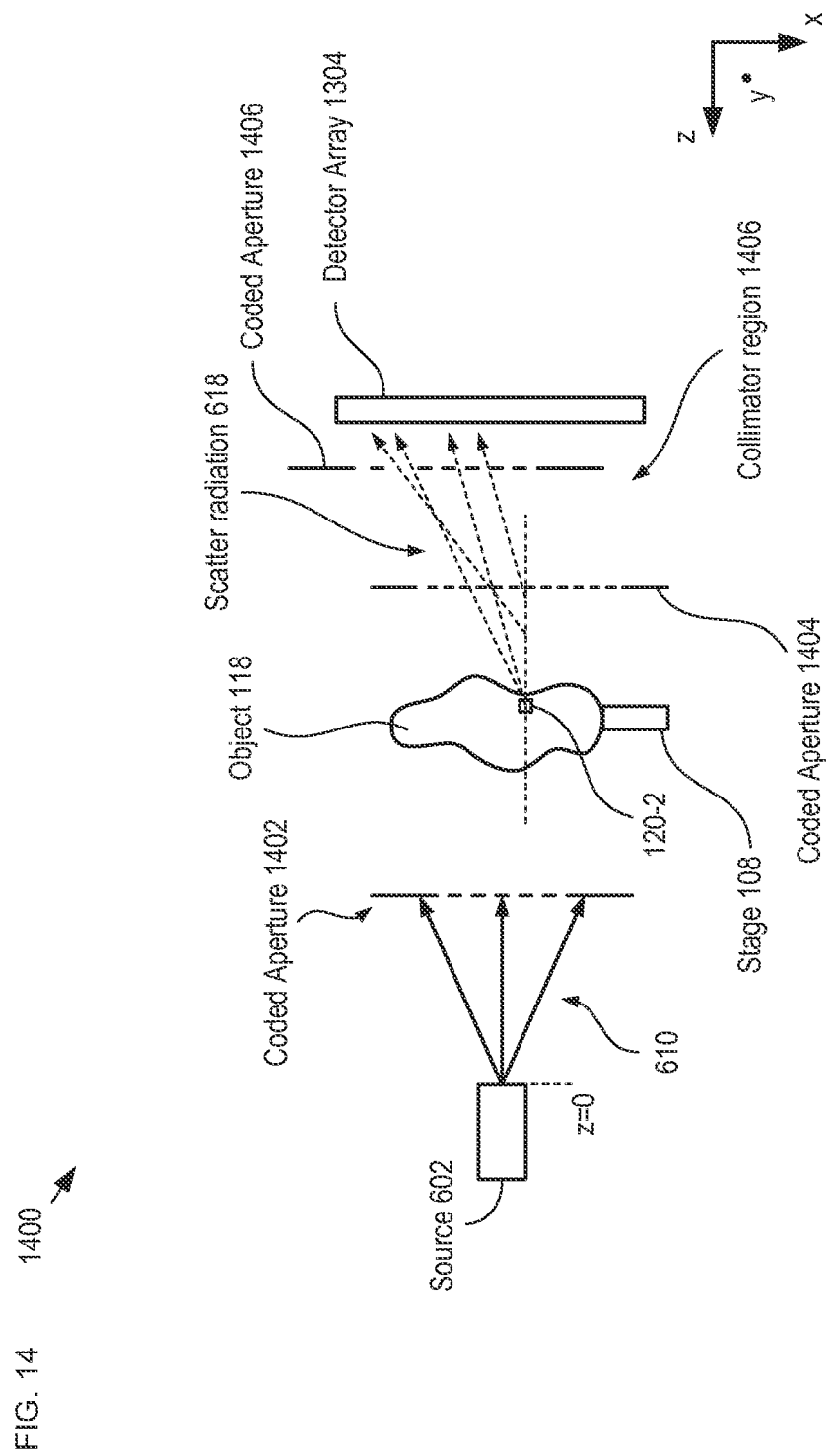
FIG. 14 depicts a schematic drawing of a molecular imaging system in accordance with a second alternative embodiment of the present invention.

In some embodiments, coded apertures 1302 and 1304 are co-designed such that the modulation contrast of the recorded signal is enhanced, thereby enabling better signal conditioning and further improved SNR, which can enable higher-fidelity estimation of large objects. In some embodiments, coded apertures 1302 and 1304 are designed to enable imaging of object 118 at a particular region-of-interest in the object. FIG. 14 depicts a schematic drawing of a molecular imaging system in accordance with a second alternative embodiment of the present invention. System 1400 includes source 602, stage 108, processor 608, coded apertures 1402, 1404, and 1406, and detector array 1304. For clarity, radiation scattered from only object feature 120-2 is depicted in FIG. 14.

One skilled in the art will recognize that a single coded aperture constrains radiation to only pass through the transparent area and block radiation incident on opaque regions. It is an aspect of the present invention that this effect can be extended by employing two or more coded apertures (or, more generally, higher-dimensional codes included fully 3-dimensional codes or spatial/spectral codes that change the spectrum in a known way at a known location) located on the detector side of an object under test such that the combination not only defines a point along a ray, but also the direction of that ray-operating essentially as a multiplexed collimator. In other words, the location of both coded apertures 1404 and 1406 between object 118 and detector array 1304 gives rise to a hybrid system that acts both as collimator and coded apertures in different regions.

Coded aperture 1402 is analogous to coded aperture 604.

Coded apertures 1404 and 1406 are designed to operate cooperatively such that the coded aperture pair are aligned to allow only scattered radiation that propagates along defined directions.

The use of multiple detector-side coded apertures offers embodiments of the present invention advantages over the prior art. First, it enables a more flexible design for the coded aperture/collimator system for feature-specific imaging. The combination of coded aperture/collimator systems can also provide more flexibility for the degree of multiplexing in the measurement.

Second, it enables a simple scheme to implement dynamic coding. To implement a time/object-dependent coded aperture is very challenging for single coded aperture. Without any modification of the physical coded aperture, but only performing mechanical movement for a single coded aperture limits the flexibility of the pattern. The combination of two coded aperture allows more complicated patterning for dynamic illumination and detection.

While scatter measurements alone are sufficient for molecular imaging, it is another aspect of the present invention that improved system performance can be realized by directly measuring the scattering electron distribution as well. In some embodiments, therefore, a detector array is included that comprises not only scatter radiation detectors, but also attenuation sensors for measuring attenuation of the primary beams (e.g., fan beams 116) as they propagate through object 118.

FIG. 15 depicts a simplified schematic drawing of a portion of a molecular imaging system in accordance with third alternative embodiment of the present invention. System 1500 includes sources 602-1 through 602-N, coded apertures 1502 and 1504, stage 108, detector array 1506, and processor 608. System 1500 employs a detector array having both scatter radiation detectors and attenuation detectors to effect more direct measurement of scatter radiation distribution.

It is an aspect of the present invention that more than one x-ray source can be used. The inclusion of multiple x-ray sources provides embodiments of the present invention with several advantages. For example, by locating multiple sources at different locations along the direction of object motion leads to an increase in the diversity of object-illumination angles. As a result, range resolution is improved since it depends on the available angular diversity and tomosynthetic reconstructions from transmission measurements. Alternatively, multiple sources located in orthogonal planes introduce illumination structures and relative source/object motion paths that are otherwise difficult to achieve using a single source. This also increases sensitivity to the presence of lower-dimensional objects (such as line and sheet objects).

Multiple sources also interrogate object 118 with multiple rays simultaneously, which increases the total scatter rate. Further, the scatter signal can be structured to maximize the amount of scatter incident on a given detector pixel, which improves SNR while also reducing the number of detector elements required.

In some embodiments, multiple sources are arranged such that the scatter signals they induce do not overlap at the same detector elements. In some embodiments, collimators are included in front of potentially overlapping detector elements to isolate one of the sources. In some embodiments, the signals from the different sources are modulated (e.g., by temporally pulsing the sources) to mitigate crosstalk.

Coded apertures 1502 and 1504 are analogous to coded aperture 604.

Detector array 1506 includes a plurality of N energy-integrating detector elements 1508-1 through 1508-N (i.e., attenuation detectors 1508), which are interleaved with a plurality of M energy-sensitive detector elements 1510-1 through 1510-M (i.e., scatter detectors 1510).

In FIG. 15, paths P and S represent possible photon paths of exemplary primary and scatter beams, respectively, from one of sources 602 (i.e., 602-1). Path P is a direct path from source 602 to detector element 1506-1. Path S is a path of an x-ray photon that interacts with a scatter point in object 118 (for clarity, only one path P and one path S is depicted and cross-talk between the scatter and attenuation signals is not shown).

Coded apertures 1502 and 1504 are designed and positioned on the source side and detector side, respectively, of object 118. In some embodiments, a coded aperture (or multiple coded apertures, as described above) is included on only the source or detector side of object 118. The coded apertures produce shadows in the vicinity of scatter detectors 1510. This prevents primary beams from saturating the scatter signals due to the relative strength of the primary path signals as compared to the scattered radiation.

It is an aspect of the present invention, as embodied by the approach depicted in FIG. 15, that it is advantageous to maximize signals along paths similar to S at the scatter detectors and P at the attenuation detectors. Although system 1500 includes coded aperture having are periodic codes, it will be clear to one skilled in the art, after reading this Specification, how to specify, make, and use alternative embodiments wherein at least one coded aperture has another code pattern. Further, one skilled in the art will recognize that, although system 1500 is a two-dimensional system, the present invention is applicable to three-dimensional systems by using 2D coded apertures and/or 2D or 3D arrangements of sources and detector elements.

It should be noted that, whether imaging 1D, 2D, or 3D objects, system 1500 can be operated in "snapshot" mode (where each pixel is exposed once) or "scanned" mode while the object is translated through the illumination (or in a mode wherein a different experimental parameter is varied to give rise to a time-dependent acquisition parameter). In general, image quality is improves as measurement diversity increases. As a result, operation of system 1500 in scanned mode is preferred for acquiring high-quality images in high dimensions.

It will be clear to one skilled in the art, after reading this Specification, that each attenuation measurement can be associated with a bundle of rays originating at the x-ray source and ending at a particular attenuation pixel where they are absorbed. In the reference frame of the object, each source follows a trajectory s(t) and each detector pixel follows a trajectory d(t), where t is a time coordinate. Let r(t)=s(t)−d(t) be the nominal ray direction for this source-detector pair. For a stationary apparatus, r=(x,y,z) is independent of time as the object translates through the illumination. If the motion follows a linear path, the attenuation time series is equivalent to a set of parallel x-ray projections. For example, let $v=v\hat{x}$ be the velocity vector along the x-direction unit vector $\hat{x}$. In this case the source trajectory is $s(t)=s_o−vt\hat{x}$ and the ray direction is fixed at r=(x,y,z). We introduce a parameterization of the measured rays via the coordinates $(\theta,\phi,\bar{x})$:

$$\theta = \tan^{-1}\left(\frac{y}{z}\right)$$

$$\phi = \tan^{-1}\left(\frac{x\cos\theta}{z}\right)$$

$$\bar{x} = \bar{x}_o = vt\cos\phi$$

where $\bar{x}_o=|s_o|\sqrt{1-(\hat{r}\cdot\hat{s}_o)^2}$ and the symbol ∧ represents a unit vector. Each value of θ defines a particular object plane P (θ) parallel to v and r. The angle φ is the in-plane angle of each ray, and $\bar{x}$ is the ray impact parameter, and together $(\phi,\bar{x})$ are the usual coordinates used for 2D Radon projections. Prior-art methods for 2D Radon imaging can be applied within each plane P (θ) to provide sufficient sampling of θ from [0,π) and x from [−R,R], where R is the radius of a sphere bounding the object. These reconstructions may be performed independently, however 3D algorithms are preferred which exploit correlations between adjacent planes in the object.

It should be further noted that x-ray projections can be significantly undersampled with minimal image degradation by using compressive reconstruction techniques. Since the numbers of sources and detectors determine the sampling rates and total coverage in $(\phi,\theta,\bar{x})$, the specific design of system 1500 depends on application-based considerations, such as the size of object 118 and desired image resolution.

Reconstruction Method Using Scatter Radiation and Attenuation

As discussed above and with respect to FIG. 1, a volumetric molecular image of object 118 can be estimated based on detected scatter signals and a forward matrix, H, where, for a given measurement, g, and forward matrix H, an estimate of the object, $f_{est}$, is obtained by solving a linear scatter model as given by Eq. (2) above. This linear scattering model relates the scatter measurements in the vector g to the object coefficients in the vector f through the forward matrix H. Solving for f in the presence of noise amounts to minimizing an objective function J=D+P, where D is a data matching or error term and P is a regularization penalty. It should be noted that any of a number of standard reconstruction algorithms that are designed to minimize j given specific choices for D and P can be used with embodiments of the present invention. The form of D is based on the expected noise statistics, and the form of P is based on prior knowledge of the object. For example, least squares estimation minimizes the error term $D=|Hf-g|^2$, which is ideal when the noise, n, is uncorrelated and follows a multivariate normal distribution with zero mean.

In the prior art, compressive reconstruction with a least-squares data term has been demonstrated and efficient algorithms have been developed for $P \propto |\Phi f|_1$, where $|v|_1 = \Sigma_i |v_i|$ is the L1-norm of some vector v and $\Phi$ is a specially chosen operator. The measurement system is regarded as compressive when the vector $\Phi f$ is sparse or otherwise compressible (meaning that the majority of the information content in $\Phi f$ lies in a relatively small number of nonzero coefficients). Common choices for D are a wavelet transform, Fourier transform, or gradient operator (for which P is called the total variation, or TV).

In cases where measurement error is shot-noise dominated, as is typical for x-ray measurements due to the high photon energy, the objective function is minimized using D as a data term that is the negative of the Poisson log likelihood: $D = -\Sigma_i [g_i \ln(Hf)_i - (Hf)_i - \ln g_i!]$, where $(Hf)_i$ and $g_i$ are the mean and noisy measurement values for index i. As discussed above and with respect to FIGS. 5A-B, minimization of this expression with respect to f can be achieved via a Poisson maximum likelihood estimation algorithm.

FIG. 16 depicts operations of a method suitable for reconstructing an image of an object based on both scatter and attenuation of x-ray radiation as it passes through the object. The use of both detected scatter and attenuation can provide improved imaging performance. A reconstruction method in accordance with the present invention is typically characterized by application-dependent and apparatus-dependent choices, including:

i. selecting the form of the data term D based on noise statistics (e.g. $D = |Hf - g|^2$ for Gaussian noise, D equals the negative log-likelihood for Poisson noise, and the like);
  ii. choosing a set of anticipated object characteristics based the application for which system 1500 is to be used (optional);
  iii. selecting the form of the regularization term P and the sparsifying basis $\Phi$ based on the set of anticipated object characteristics (e.g. L1-norm for sparse objects, TV-norm for piecewise smooth objects, wavelet, Fourier, or canonical bases for $\Phi$);
  iv. selecting the form of the forward matrix H based on the relevant physical parameters of the imaging system, such as component locations, orientations, spatial/temporal/energy response, sampling rates, etc.; and
  v. selecting a mathematical reconstruction algorithm based on the form of the objective function J=D+P and the desired computational efficiency of the reconstruction. It should be noted that, in some embodiments, the choice of algorithm also determines the manner in which H is used to update the estimate of the desired image f. Examples of suitable unregularized (P=0) least squares algorithms are the Moore-Penrose pseudoinverse, Gauss-Newton, Gauss-Seidel, or a number of quasi-Newton methods. For regularization with the L1-norm, suitable algorithms include the Lasso method, IST and variants (TwIST, ISTA), and L1 Magic. Suitable algorithms for the data term taking the form of a negative log likelihood include Poisson MLE, alternating minimization, and and the like.

Method 1600 is described with reference to FIG. 15 and begins with operation 1601, wherein attenuation detectors 1508 capture superimposed projections from sources 602-1 through 602-N (referred to, collectively, as sources 602).

At operation 1602, scatter detectors 1510 capture scatter radiation from a subset of sources 602. For exemplary purposes, in this embodiments, N is equal to 2 and attenuation detectors 1508 capture projections from both sources, while scatter detectors 1510 capture scatter radiation from only one source (e.g., source 602-1). Further, in this example, attenuation detectors 1508 capture the projections at each of 1000 frames, while scatter detectors 1510 capture scatter radiation only during the first 152 of these frames.

At operation 1603, processor 608 performs a series of reconstructions for a series of different combinations of data using an unregularized Poisson MLE algorithm. Each reconstruction proceeds until the objective function stopped changing by more than a user-defined percentages (e.g., 2%) between each iteration. Included in the series of reconstructions are both an "attenuation-only reconstruction" (i.e., a reconstruction based only on attenuation data) and a "scatter-only reconstruction" (i.e., a reconstruction based on only on scatter data). Although this exemplary method employs an unregularized Poisson MLE algorithm, it will be clear to one skilled in the art, after reading this Specification, how to practice the present invention using another method—for example, the unregularized Poisson MLE algorithm can be modified for a specific use, such as regularizing by introducing a nonzero penalty P, and adapting the Poisson noise model to Gaussian statistics or other measurement error models informed by the measured data and underlying physics of signal generation and detection.

At optional operation 1604, processor 608 performs a density-constrained reconstruction by thresholding the density from the attenuation-only reconstruction at another user-defined percentage (e.g., 15%) of its maximum value, and where the scatter data is only allowed to influence white pixels in the image domain. It should be noted that operation 1604 is not necessary when the reconstruction performed in operation 1603 provides sufficient image quality, which is based on the application for which the imaging system is intended.

FIGS. 17A, 17B, and 17C depict a modified Shepp-Logan phantom-based test object, a reconstruction using a density-constrained attenuation-only data set, and a reconstruction using a density-constrained attenuation and scatter data set, respectively.

Plot 1700 shows a gray-scale-coded map of the material composition of the test object. Plot 1702 shows a histogram of total concentrations, arranged in order of density, of the test object. The test object is simulated as consisting of 4 materials, but a total of 18 possible materials were used in the simulation and so they are also shown in plot 1702. The object domain is a square area in the x-y plane with sides of length 64 mm. The object was pixelated at a resolution of 32×32, giving a voxel sampling rate of 2×2 mm.

Plot 1704 shows a gray-scale-coded map of estimated material composition of the test object using attenuation data alone, as described above. Plot 1704 demonstrates that an attenuation-only reconstruction correctly localizes electron density but it can be seen from plot 1706 that this approach results in poor material discrimination.

Plot 1708 shows a gray-scale-coded map of estimated material composition of the test object using a density-constrained reconstruction that was performed by thresholding the density from the attenuation-only reconstruction (as in plot 1704) at 15% of its max value to produce a voxel mask, where the scatter data was only allowed to influence white pixels (which constitute about 24% of the image domain). Plot 1710 demonstrates that this approach maintains the sharpness of the heterogeneous reconstruction but at the cost of missing some of the lower-density materials. These results demonstrate the power of joint attenuation and scatter measurement, however, where the results are achieved by two different processes, namely "density-constrained reconstruction" and "heterogeneous reconstruction."

One skilled in the art will recognize, after reading this Specification, that the geometry of system 1500 is just one of many geometries for an x-ray system operative for acquiring and combining information from both attenuation and scatter measurements. It should be noted that the number of sources and detectors, the design of the coded apertures, and the acquisition settings are design parameters that are based on the application for which system 1500 is intended.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. An imaging system operative for estimating the molecular structure of an object, the imaging system comprising:
    a first source that is configured to provide a first radiation beam;
    a first coded aperture, the first coded aperture being configured to modulate the first radiation beam to provide a first plurality of beam elements;
    a means for changing the interaction between the first plurality of beam elements and the object in a time-dependent manner; and
    a detector that is configured to receive radiation based on each of the plurality of beam elements, the detector including a first detector element that is an energy-sensitive detector element, the first detector element being arranged to receive scatter radiation from the object, wherein the detector provides an output signal that is based on the received radiation, and wherein the output signal is a temporally resolved signal.

2. The imaging system of claim 1 wherein the means for changing the interaction between the first plurality of beam elements and the object comprises a stage for moving at least one of the source and the object.

3. The imaging system of claim 1 further comprising a processor, the processor being configured to receive the output signal and compute an estimate of the molecular structure of the object, wherein the estimate is based on a reconstruction that is based on a forward model of the imaging system, and wherein the forward model accounts for both radiation scatter and radiation attenuation by the object.

4. The imaging system of claim 1 further comprising a second coded aperture, wherein the first coded aperture is located between the first source and the object and the second coded aperture is located between the object and the detector.

5. The imaging system of claim 4 further comprising a third coded aperture that is located between the second coded aperture and the detector.

6. The imaging system of claim 1, wherein the first coded aperture includes a code that is controllable.

7. The imaging system of claim 1, wherein the detector further includes a second detector element that is an energy-integrating detector element, the second detector element being arranged to receive non-scattered radiation from the object during the first time period.

8. The imaging system of claim 1 wherein the first source comprises a second source and a third source that are configured to collectively provide the first radiation beam.

9. The imaging system of claim 1, wherein the detector comprises a first plurality of detector elements, each of which is an energy-sensitive detector element, the first plurality of detector elements including the first detector element.

10. The imaging system of claim 9, wherein the first plurality of detector elements is arranged in a linear array that is aligned along a first direction.

11. The imaging system of claim 10, wherein the stage is operative for inducing the relative motion such that it is a linear motion aligned along a first direction.

12. The imaging system of claim 10, wherein the stage is operative for inducing the relative motion such that it is a linear motion aligned along a second direction that is orthogonal to the first direction.

13. The imaging system of claim 9, wherein the first plurality of detector elements is arranged in two-dimensional arrangement.

14. The imaging system of claim 13, wherein the two-dimensional arrangement includes two broken, non-overlapping linear arrays of detector elements.

15. The imaging system of claim 13, wherein the two-dimensional arrangement is non-periodic in each dimension.

16. The imaging system of claim 1, wherein the first coded aperture is configured to spatially modulate the first radiation beam in two dimensions.

17. The imaging system of claim 16, wherein the first coded aperture includes an arrangement of features arranged in a two-dimensional arrangement, the arrangement being aperiodic in at least one of the two dimensions.

18. The imaging system of claim 16, wherein the first coded aperture includes an arrangement of features arranged in a two-dimensional arrangement, the arrangement being aperiodic in each of the two dimensions.

19. The imaging system of claim 1, wherein the first source is configured to provide the first radiation beam as polychromatic radiation.

* * * * *